United States Patent
Guerin-Marchand et al.

(10) Patent No.: US 7,438,917 B2
(45) Date of Patent: *Oct. 21, 2008

(54) **PEPTIDE SEQUENCES SPECIFIC FOR THE HEPATIC STAGES OF *P. FALCIPARUM* BEARING EPITOPES CAPABLE OF STIMULATING THE T LYMPHOCYTES**

(75) Inventors: Claudine Guerin-Marchand, Paris (FR); Pierre Druilhe, Paris (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/404,777

(22) Filed: Apr. 17, 2006

(65) Prior Publication Data

US 2006/0182769 A1 Aug. 17, 2006

Related U.S. Application Data

(62) Division of application No. 09/837,344, filed on Apr. 19, 2001, now Pat. No. 7,087,231, which is a division of application No. 08/462,625, filed on Jun. 5, 1995, now Pat. No. 6,319,502, which is a division of application No. 08/098,327, filed as application No. PCT/FR92/00104 on Feb. 5, 1992, now Pat. No. 6,270,771.

(30) Foreign Application Priority Data

Feb. 5, 1991 (FR) .................................. 91 01286

(51) Int. Cl.
*A61K 39/00* (2006.01)
*A61K 39/015* (2006.01)
*A61K 39/002* (2006.01)
*A61K 38/00* (2006.01)
*A61K 38/04* (2006.01)
*A01N 37/18* (2006.01)
*C07K 16/00* (2006.01)
*C07K 17/00* (2006.01)
*C07K 7/00* (2006.01)
*C07K 14/00* (2006.01)
*C07K 5/00* (2006.01)
*C07K 2/00* (2006.01)
*C07K 4/00* (2006.01)
*C12Q 1/00* (2006.01)
*G01N 33/53* (2006.01)
*G01N 33/567* (2006.01)
*G01N 33/543* (2006.01)

(52) U.S. Cl. .............. 424/191.1; 424/184.1; 424/185.1; 424/192.1; 424/265.1; 424/268.1; 424/272.1; 530/300; 530/350; 530/324; 530/325; 530/326; 530/344; 530/822; 530/820; 435/4; 435/7.1; 435/7.2; 435/7.92

(58) Field of Classification Search ................ None
See application file for complete search history.

(56) References Cited

U.S. PATENT DOCUMENTS

| | | | |
|---|---|---|---|
| 5,589,343 A | 12/1996 | Marchand et al. | |
| 5,599,542 A | 2/1997 | Marchand et al. | |
| 5,602,031 A | 2/1997 | Marchand et al. | |
| 5,690,941 A | 11/1997 | Druilhe et al. | |
| 5,928,901 A | 7/1999 | Marchand et al. | |
| 6,017,538 A | 1/2000 | Druilhe et al. | |
| 6,191,270 B1 | 2/2001 | Druilhe et al. | |
| 6,270,771 B1 | 8/2001 | Guerin-Marchand et al. | |
| 6,319,502 B1 | 11/2001 | Guerin-Marchand et al. | |
| 6,669,945 B1 | 12/2003 | Nardin et al. | |
| 6,828,416 B1 * | 12/2004 | Lal et al. ..................... | 530/300 |
| 7,056,518 B2 * | 6/2006 | Druilhe et al. ............ | 424/191.1 |
| 7,087,231 B2 * | 8/2006 | Guerin-Marchand et al. ........................ | 424/191.1 |
| 7,332,595 B2 * | 2/2008 | Guerin-Marchand et al. ........................ | 536/23.7 |
| 2002/0041882 A1 | 4/2002 | Guerin-Marchand et al. | |
| 2003/0064075 A1 | 4/2003 | Guerin-Marchand et al. | |

(Continued)

FOREIGN PATENT DOCUMENTS

EP 0 407 230 1/1991

(Continued)

OTHER PUBLICATIONS

Rzepczyk et al, J. Immunology, 1988, 141/9:3197-3202.*

(Continued)

*Primary Examiner*—N. M Minnifield
(74) *Attorney, Agent, or Firm*—Crowell & Moring LLP

(57) ABSTRACT

The present invention relates to an in vitro diagnostic method for malaria in an individual comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed. The invention further relates to a polypeptide comprising at least one T epitope from a liver-stage specific protein produced by *P. falciparum* and a vaccine composition directed against malaria comprising a molecule having one or more peptide sequences bearing all or part of one or more T epitopes resulting from the infectious activity of *P. falciparum* in the hepatic cells.

2 Claims, 18 Drawing Sheets

U.S. PATENT DOCUMENTS

| | | | |
|---|---|---|---|
| 2004/0067236 A1 | 4/2004 | Cohen et al. | |
| 2005/0075496 A1* | 4/2005 | Druilhe et al. | 536/23.7 |
| 2005/0108791 A1 | 5/2005 | Edgerton | |
| 2005/0266017 A1 | 12/2005 | Druilhe et al. | |
| 2005/0287166 A1* | 12/2005 | Druilhe et al. | 424/191.1 |
| 2006/0182769 A1* | 8/2006 | Guerin-Marchand et al. | 424/272.1 |
| 2006/0188527 A1* | 8/2006 | Hoffman et al. | 424/272.1 |

FOREIGN PATENT DOCUMENTS

| | | |
|---|---|---|
| WO | WO 84/02917 A1 * | 8/1984 |
| WO | 86/01802 A1 | 3/1986 |
| WO | WO 86/01802 A1 * | 3/1986 |
| WO | WO 86/06075 A1 * | 10/1986 |
| WO | WO 87/05607 A1 * | 9/1987 |
| WO | 88/05785 A1 | 8/1988 |
| WO | 90/06130 A1 | 6/1990 |
| WO | 92/05193 A1 | 4/1992 |
| WO | 92/13884 A1 | 8/1992 |
| WO | 84/02917 A1 | 8/1994 |

OTHER PUBLICATIONS

Russo et al, J. Immunology, 1989, 143/2:655-659.*
Calvo-Calle, Dissertation Abstracts International, 2004, 65/9B:4495 abstract only.*
Perlaza et al, Eur. J. Immunol., 2001, 31:2200-2209.*
BenMohamed et al, Infection and Immunity, 2004, 72/8:4376-4384.*
Herbert et al, J. Immunological Methods, 2003, 275:123-132.*
Brahimi et al, Infection and Immunity, 2001, 69/6:3845-3852.*
Calvo-Calle et al, J. Immunology, 2005, 175:7575-7585.*
Taylor-Robinson, Immunologic Research, 2003, 27/1:53-69.*
Taylor-Robinson, Expert Rev. Vaccines, 2002, 1/3:317-340.*
Hoffman et al, In: Technological Advances in Vaccine Development, 1988, pp. 625-639.*
Favaloro et al, Nucleic Acids Research, 1986, 14/21:8265-8277.*
Guerin-Marchand, C., et al., *Nature*, 1987, 329/6135:164-7, Macmillan Publishers, USA.
Londono, J., et al., *J. Immunol.*, 1990, 145(5):1557-63, American Association of Immunologists, USA.
Hollingdalte, M., et al., *Chem Abst.*, 1990, 113:189314w, pp. 534, American Chemical Society, USA.
Marchand, C., et al., *Bulletin of the World Health Organization*, 1990, 68:158-64.
Favalero, J.M., et al., *Nucl. Acid Res.*, 1986, 14(1):8265-77, Oxford University Press, Great Britain.
Ben-Mohamed et al., *Eur. J. Immunol.*, 1997, 27:1242-53, Wiley-VCH Verlag GmbH, Germany.
Sharma, Shobhona, et al., "Diversity of Circumsporozoite Antigen Genes from Two Strains of the Malarial Parasite *Plasmodium knowlesi*", *Science*, Aug. 1985, pp. 779-782, vol. 229, AAAS, Washington, D.C.
Druilhe, P., et al., "Species- and Stage-Specific Antigens in Exoerythrocytic Stages of *Plasmodium falciparum*", *Am. J. Trop. Med. Hyg.*, 1984, pp. 336-341, 33(3), The American Society of Tropical Medicine and Hygiene, US.
Weber, James L., et al., "Primary Structure of a *Plasmodium falciparum* Malaria Antigen Located at the Merozoite Surface and Within the Parasitophorous Vacuole", *J. Biol. Chem.*, Aug. 15, 1988, pp. 11421-11425, vol. 263, No. 23, American Society for Biochemistry and Molecular Biology, Baltimore, MD.
Fidock, David A., et al., "*Plasmodium falciparum* Liver Stage Antigen 1- is Well Conserved and Contains Potent B and T Cell Determinants", *J. Immunol.*, 1994, pp. 190-204, vol. 153, The American Association of Immunologists, Baltimore, MD.
Zhu, Jingdong, et al., "Structure of *Plasmodium falciparum* liver stage antigen-1", *Molecular and Biochemical Parasitology*, 1991, pp. 223-226, vol. 48, Elsevier Science Publisher B.V., Amersterdam, The Netherlands.

Shortt, H. E., et al., "The Pre-Erythrocytic Development of *Plasmodium gynomolgi* and *Plasmodium vivax*", *Transactions of the Royal Society of Tropical Medicine and Hygiene.*, May 1948, pp. 785-795, vol. 41, No. 6, UK.
Roitt, Ivan, et al., *Immunology*, 1989, pp. 2.4-2.7, 2nd Edition, Gower Medical Publishing, London, England.
"B cell epitope prediction reviews","Other B cell epitope prediction" and "T cell epitopes and prediction", ePitope Informatics, Prediction and analysis of protein epitopes, http://www.epitope-informatics.com/References.htm.
Margalit, H., et al., "Prediction of immunodominant helper T cell antigenic sites from the primary sequence.", *J Immunol.* Apr. 1, 1987;138(7):2213-29.; PMID: 2435793 [PubMed—indexed for Medline]; http://www.ncbi.nlm.nih.gov/entrez/query.fcgi?cmd=Retrieve&db=PubMed&list_ui...; Aug. 3, 2004 (Abstract only).
Livingstone, AM, et al., "The structure of T-cell epitopes.", *Annu Rev Immunol.* 1987;5:477-501.; PMID: 2439104 [PubMed—indexed for Medline]; http:/www.ncbi.nlm.nih.gov/entrez/query.fcgi?cmd=retrieve&db=pubmed&dopt=A...; Aug. 3, 2004 (Abstract only).
Spouge, JL, et al., "Strong conformational propensities enhance T cell antigenicity.", *J Immunol.* Jan. 1, 1987;138(1):204-12; PMID: 2431054 [PubMed—indexed for Medline]; http://www.ncbi.nlm.nih.gov/entrez/query.fcgi?cmd=Retrieve&db-PubMed&list_uni... Aug. 3, 2004 (Abstract only).
Jolivet, M., et al., "Polyvalent synthetic vaccines: relationship between T epitopes and immunogenicity.", *Vaccine.* Feb. 1990;8(1):35-40.; PMID: 1690488 [PubMed—indexed for Medline]; http://www.ncbi.nlm.nih.gov/entrez/query.fcgi?cmd=Retrieve&db=PubMed&list_ui... Aug. 3, 2004 (Abstract only).
Miles, MA, et al., "Cloning of microbial epitopes relevant for T- and B-cells.", *Behring Inst Mitt.* Feb. 1991;(88):133-41.; PMID: 1710887 [PubMed—indexed for Medline]; http://www.ncbi.nlm.nih.gov/entrez/query.fcgi?cmd=Retrieve&db=PubMed&list_ui... Aug. 3, 2004 (Abstract only)....
Miles, MA, et al., "Cloning of microbial epitopes relevant for T- and B-cells.", *Behring Inst Mitt.* Feb. 1991;(88):133-41.; PMID: 1710887 [PubMed—indexed for Medline]; http://www.ncbi.nlm.nih.gov/entrez/query.fcgi?cmd=Retrieve&db=PubMed&list_ui... Aug. 3, 2004 (Abstract only).
Feller, DC, "Identifying antigenic T-cell sites.", *Nature.* Feb. 21, 1991;349(6311):720-1.; PMID: 1705016 [PubMed—indexed for Medline]; http://www.ncbi.nlm.nih.gov/entrez/query.fcgi?cmd=Retrieve&db=PubMed&list_ui... Aug. 3, 2004 (Abstract only).
Van der Zee, R., et al., "Efficient mapping and characterization of a T cell epitope by the simultaneous synthesis of multiple peptides.", *Eur J Immunol.* Jan. 1989;19(1):43-7.; PMID: 2465904 [PubMed—indexed for Medline]; http://www.ncbi.nlm.nih.gov/entrez/query.fcgi?cmd=Retrieve&db=PubMed&list_ui... Aug. 3, 2004 (Abstract only).
Rotzschke, O., et al., "On the nature of peptides involved in T cell alloreactivity.", *J Exp Med.* Nov. 1, 1991;174(5):1059-71.; PMID: 1940788 [PubMed—indexed for Medline]; http://www.ncbi.nlm.nih.gov/entrez/query.fcgi?cmd=Retrieve&db=PubMed&list_ui... Aug. 3, 2004 (Abstract only).
Rotzschke, O., et al., "Exact prediction of a natural T cell eiptope.", *Eur J Imunol.* Nov. 1991;21(11):2891-4.; PMID: 1718764 [PubMed—indexed for Medline]; http://www.ncbi.nlm.nih.gov/entrez/query.fcgi?cmd=Retrieve&db=PubMed&list_ui... Aug. 3, 2004 (Abstract only).
Perlaza, Blanca Liliana, et al., "Immunogenicity of Four *Plasmodium falciparum* Preerythrocytic Antigens in *Aotus lemurinus* Monkeys", *Infection and Immunity*, Jul. 1998, pp. 3423-3428, vol. 66, No. 7, American Society for Microbiology, Washington, D.C. (PMID: 9632616—PubMed Abstract attached).
Shi, Ya Ping, et al., "Immunogenicity and in vitro protective efficacy of a recombinant multistage *Plasmodium falciparum* candidate vaccine", *PNAS.—Medical Sciences*, Feb. 1999, pp. 1615-1620, vol. 96, National Academy of Sciences, Washington, DC.

Kurtis, Jonathan D., et al., "Pre-erythrocytic immunity to *Plasmodium falciparum*: the case for an LSA-1 vaccine", *Trends in Parasitology*, May 2001, pp. 219-223, vol. 17, No. 5, Elsevier Science Ltd., England.

Heal, Karen G., et al., "Expression and immunogenicity of a liver stage malaria epitope presented as a foreign peptide on the surface of RNA-free MS2 bacteriophage capsids", *Vaccine*, 1999, pp. 251-258, vol. 18, Elsevier Science Ltd., England.

Joshi, Sunil K., et al., "Analysis of Immune Responses against T- and B-Cell Epitopes from *Plasmodium falciparum* Liver-Stage Antigen 1 in Rodent Malaria Models and Malaria-Exposed Human Subjects in India" *Infection and Immunity*, Jan. 2000, pp. 141-150, vol. 68, No. 1, American Society for Microbiology, Washington, D.C.

Kurtis, Jonathan D., et al., "Interleukin-10 Responses to Liver-Stage Antigen 1 Predict Human Resistance to *Plasmodium falciparum*", *Infection and Immunity*, Jul. 1999, pp. 3424-3429, vol. 67, No. 7, American Society for Microbiology, Washington, D.C.

Phillips, R.S., "Malarial vaccines—a problem solved or simply a promising start?", *Protozoological Abstracts*, Nov. 1994, pp. 459-488, vol. 18, No. 11, CAB International, Oxfordshire, UK.

Cox, F.E.G., "Another route to a vaccine?", *Nature*, Dec. 1992, pp. 417-418, vol. 360, Nature Publishing Group, London, England.

Taylor-Robinson, Andrew W., et al., "Candidacy of liver stage antigen-1 for *Plasmodium falciparum* vaccine development", *J. Protozoology Research*, 2001, pp. 1-18, vol. 11, National Research Center for Protozoan Diseases, JP.

"Clinical Trials: Crucial Steps on the Road to a Malaria Vaccine", Malaria vaccine initiative Technical Series, Aug. 2004, pp. 1-5, www.malariavaccine.org, Rockville, MD.

*Immune Response System*, cite maintained by Robert J. Husker, Ph.D., last updated Dec. 4, 1998.

Fidock, D.A., et al., "*Plasmodium falciparum* Liver Stage Antigen-1 Is Well Conserved and Contains Potent B and T Cell Determinants[1]", *J. Immunol.*, Jul. 1994, pp. 190-204; 153, The American Association of Immunologists, Baltimore, MD.

*State of the art of new vaccines: research & development*, pp. 1-6, Initiative for Vaccine Research website, http://www.who.int/vaccine_research/documents/new_vaccines/en/i..., Who, 2005.

Gardner, Malcolm J., et al., "Genome Sequence of the human malaria parasite *Plasmodium falciparum*", *Nature*, 2002 (Rec'd Jul. 31, 2002 and Accepted Sep. 25, 2002), pp. 498-511, 419, Nature Publishing Group, London, England.

Hillier, Collette J., et al., "Process Development and Analysis of Liver-Stage Antigen 1, a Preerythrocyte-Stage Protein-Based Vaccine for *Plasmodium falciparum*", *Infection and Immunity*, Apr. 2005, pp. 2109-2115, vol. 73, No. 4, American Society for Microbiology, Washington, D.C.

Yang, et al., "Sequence variations in the non-repetitive regions of the liver stage-specific antigen-1 (LSA-1) of *Plasmodium falciparum* from field isolates", *Molecular and Biochemical Parasitology*, 1995 (Rec'd Jan. 12, 1995 and Accepted Mar. 27, 1995), pp. 291-294, 71, Elsevier Science B.V., Amsterdam, The Netherlands.

Reddy, G. Roman, et al., "Gene sequence tags from *Plasmodium falciparum* genomic DNA fragments prepared by the "genease" activity of mung bean nuclease", *PNAS—Genetics*, Nov. 1993, pp. 9867-9871, vol. 90, National Academy of Sciences, Washington, D.C.

\* cited by examiner

```
(5')   1  SDLEQERRAKEKLQEQQ
      18  SDLEQDRLAKEKLQEQQ
      35  SDLEQERLAKEKLQEQQ
      52  SDLEQERRAKEKLQEQQ
      69  SDLEQERRAKEKLQEQQ
      86  SDLEQDRLAKEKLQEQQ
     103  SDLEQERRAKEKLQEQQ
     120  SDLEQERKAKEKLQEQQ
     137  SDLEQERLAKEKLQEQQ
     154  SDLEQERRAKEKLQEQQ
     171  SDLEQERRAKEKLQEQQ
     188  SDLEQERRAKEKLQEQQ
     205  RDLEQ

210  RKADTKKNLERKKEHGDILAEDLYGRLEIP
     240  AIELPSENERGYYIPHQSSLPQDNRGNSRD
     270  SKEISIIEKTNRESITTNVEGRRDIHKGHL
     300  EEKKDGSIKPEQKEDKS    316 (3')
```

FIGURE 1

(5') 1    AAAGCGGATCTAGAACAAGAGAGACGTGCTAAAGAAAAGTTGCAAGAACAAC
     52   AAAGCGGATTTAGAACAAGAGAGATAGACTTGCTAAAGAAAAGTTACAAGAGCAGC
     103  AAAGCGGATTTAGAACAAGAGAGACTTGCTAAAGAAAAGTTGCAAGAACAAC
     154  AAAGCGGATCTAGAACAAGAGAGAGACGTGCTAAAGAAAAGTTGCAAGAACAAC
     205  AAAGCGGATTTAGAACAAGAGAGAGACGTGCTAAAGAAAAGTTGCAAGAACAAC
     256  AAAGCGGATTTAGAACAAGATAGACTTGCTAAAGAAAAGTTACAAGAGCAGC
     307  AAAGCGGATTTAGAACAAGAGAGACGTGCTAAAGAAAAGTTGCAAGAACAAC
     358  AAAGCGGATTTAGAACAAGAGAGACGTGCTAAAGAAAAGTTGCAAGAACAAC
     409  AAAGCGGATTTAGAACAAGAGAGACTTGCTAAAGAAAAGTTGCAAGAACAAC
     460  AAAGCGGATTTAGAACAAGAGAGACGTGCTAAAGAAAAGTTGCAAGAACAAC
     511  AAAGCGGATTTAGAACAAGAGAGACGTGCTAAAGAAAAGTTGCAAGAACAAC
     562  AAAGCGGATTTAGAACAAGAGAGACGTGCTAAAGAAAAGTTGCAAGAGCAGC
     613  AAAGAGATTTAGAACAA
     630  AGGAAGGCTGATACGAAAAAAATTTAGAAAGAAAAAGGAACATGGAGAT
     681  ATATTAGCAGAAAATTTATATGGTCGTTTAGAAATACCAGCTATAGAACTT
     732  CCATCAGAAAATGAACGTGGATATATTATATACCACATCAATCTTCTTTACCT
     783  CAGGACAACAGAGGGAATAGTAGAGATTCCAAGGAAATATCTATAATAGAA
     834  AAAACAAATAGAGAATCTATTACAACAAATGTTGAAGGACGAAGGGATATA
     885  CATAAAGGACACTCTTGAAGAAAAAGAAAGATGGTTCAATAAAACCAGAACAA
     936  AAAGAAGATAAATCT   950 (3')

FIGURE 2

RDELFNELLNSVDVNGEVKENILEESQVNDDIFNSLVKSVQQEQQ
HNVEEKVEESVEENDEESVEENVEENVEENDDGSVASSVEESI
ASSVDESIDSSIEENVAPTVEEIVAPTVEEIVAPSVVEKCAPSVE
ESVAPSVEESVAEMLKER

FIGURE 3

5' GAA TTC CGT GAT GAA CTT TTT AAT GAA TTA TTA AAT AGT GTA GAT
GTT AAT GGA GAA GTA AAA GAA AAT ATT TTG GAG GAA AGT CAA GTT AAT
GAG GAT ATT TTT AAT AGT TTA GTA AAA AGT GTT CAA CAA GAA CAA CAA
CAC AAT GTT GAA GAA AA AGT TGA AGA AAG TGT AGA AGA AA ATG ACG
AAG AAA GTG TAG AAG AAA ATG TAG AAG AAA ATG TAG AAG AAA ATG
ACG ACG GAA GTG TAG CCT CAA GTG TTG AAG AAA GTA TAG CTT CAA GTG
TTG ATG AAA GTA TAG ATT CAA GTA TTG AAG AAA ATG TAG CTC CAA CTG
TTG AAG AAA TCG TAG CTC CAA CTG TTG AAG AAA TTG TAG CTC CAA GTG
TTG TAG AAA AGT GTG CTC CAA GTG TTG AAG AAA GTG TAG CTC CAA GTG
TTG AAG AAA GTG TAG CTG AAA TGT TGA AGG AAA GGA ATT C 3'

FIGURE 4

```
                                                    LSA-TER
                                                    729S-NRI
                                                    729S-NRII
                           NSRDSKEISIIEKTNRESITTNVEGRRDIHK   729S-Rep

DELFNELLNSVDVDVNGEVKENILEESQ
LEESQVNDDIFSNSLVKSVQQEQHNV
VEKCAPSVEESVAPSVEESVAEMLKER
```

FIGURE 5

NUCLEOTIDE SEQUENCE OF THE LSA GENE
5' END (NON-CODING 5' END)

1    AAAGTATACATCTTCCTTCTTTACTTCTTAAA (CODING 5' END, UNIQUE)

33   ATGAAACATATTTTGTACATATCATTTTACTTTATCCTTGTTAATTTATTG
84   ATATTTCATATAAATGGAAAGATAATAAAGAATTCTGAAAAAGATGAAATCA
135  TAAAATCTAACTTGAGAAGTGGTTCTTCAAATTCTAGGAATCGAATAAATGA
186  GGAAAATCACGAGAAGAAACACGTTTTATCTCATAATTCATATGAGAAAACT
237  AAAAATAATGAAAATAATAAATTTTTCGATAAGGATAAAGAGTTAACGATGT
288  CTAATGTAAAAAATGTGTCACAAACAAATTTCAAAGTCTTTTAAGAAATCT
339  TGGTGTTTCAGAGAATATATTCCTTAAAGAAAATAAATTAAATAAGGAAGGG
390  AAATTAATTGAACACATAATAAATGATGATGACGATAAAAAAAAATATATTA
441  AAGGGCAAGACGAAAACAGACAAGAAGATCTTGAAGAAAAAGCA (CODING 5' END, repetitive)

492  GCTAAAGAAAAGTTACAGGGGCAACAAAGCGATTCAGAACAAGAGAGACGT
543  GCTAAAGAAAAGTTGCAAGAACAACAAAGCGATTTAGAACAAGAGAGACTT
594  GCTAAAGAAAAGTTGCAAGAACAACAAAGCGATTTAGAACAAGAGAGACGT
645  GCTAAAGAAAAGTTGCAAGAACAACAAAGCGATTTAGAACAAGAGAGACTT
696  GCTAAAGAAAAGTTGCAAGAACAACAAAGCGATTTAGAACAAGAGAGACGT
747  GCTAAAGAAAAGTTGCAAGAACAACAAAGCGATTTAGAACAAGAGAGACGT
798  GCTAAAGAAAAGTTGCAAGAACAACAAAGCGATTTAGAACAAGAGAGACTT
849  GCTAAAGAAAAGTTACAAGAGCAGCAAAGCGATTTAGAACAAGATAGACTT
900  GCTAAAGAAAAGTTGCAAGAACAACAAAGCGATTTAGAACAAGAGAGACGT
951  GCTAAAGAAAGGTTGCAAGAACAACAAAGCGATTTAGA 988

FIGURE 6

LSA.5'/ATG - -> 1-phase Translation

DNA sequence 956 b.p. ATGAAACATATT ... AAGCGATTTAGA linear

```
  1 /   1                                                                    31 /  11
ATG AAA CAT ATT TTG TAC ATA TCA TTT TAC ATA TCT CTT GTT AAT TTA TTG ATA TTT CAT
met lys his ile leu tyr ile ser phe tyr ile leu val asn leu leu ile phe his
 61 /  21                                                                    91 /  31
ATA AAT GGA AAG ATA ATA AAG AAT TCT GAA AAA GAT GAA ATC ATA AAA TCT AAC TTG AGA
ile asn gly lys ile ile lys asn ser glu lys asp glu ile ile lys ser asn leu arg
121 /  41                                                                   151 /  51
AGT GGT TCT TCA AAT TCT AGG AAT CGA AAT AGT GAG GAA AAT CAC GAG AAG AAA CAC GTT
ser gly ser ser asn ser arg asn arg asn ser glu glu asn his glu lys lys his val
181 /  61                                                                   211 /  71
TTA TCT CAT AAT TCA TAT GAG GAG AAA ACT AAA AAT GAA AAT AAT AAA TTT TTC GAT AAG
leu ser his asn ser tyr glu glu lys thr lys asn glu asn asn lys phe phe asp lys
241 /  81                                                                   271 /  91
GAT AAA GAG TTA ACG ATG TCT AAT GTA AAA AAT GTG TCA CAA ACA AAT TTC AAA AGT CTT
asp lys glu leu thr met ser asn val lys asn val ser gln thr asn phe lys ser leu
301 / 101                                                                   331 / 111
TTA AGA AAT CTT GGT GTT TCA GAG AAT ATA TTC CTT AAA GAA AAT AAA TTA AAT AAG GAA
leu arg asn leu gly val ser glu asn ile phe leu lys glu asn lys leu asn lys glu
```

FIGURE 7A

```
361 /  121                           391 /  131
GGG AAA TTA ATT GAA CAC ATA ATA AAT GAT GAC GAT AAA AAA TAT ATT AAA GGG
gly lys leu ile glu his ile ile asn asp asp asp lys lys tyr ile lys gly
421 /  141                           451 /  151
CAA GAC GAA AAC AGA CAA GAA GAT CTT GAA AAA GCA GCT AAA GAA AAG TTA CAG GGG
gln asp glu asn arg gln glu asp leu glu lys ala ala lys glu lys leu gln gly
481 /  161                           511 /  171
CAA CAA AGC GAT TCA GAA CAA CAA AGA CGT GCT AAA GAA AAG TTG CAA GAA CAA AGC
gln gln ser asp ser glu gln gln arg arg ala lys glu lys leu gln glu gln ser
541 /  181                           571 /  191
GAT TTA GAA CAA GAG AGA CTT GCT AAA GAA AAG TTG CAA GAA CAA CAA AGC GAT TTA GAA
asp leu glu gln glu arg leu ala lys glu lys leu gln glu gln gln ser asp leu glu
601 /  201                           631 /  211
CAA GAG AGA CGT GCT AAA GAA AAG TTG CAA GAA CAA CAA AGC GAT TTA GAA CAA GAG AGA
gln glu arg arg ala lys glu lys leu gln glu gln gln ser asp leu glu gln glu arg
661 /  221                           691 /  231
CTT GCT AAA GAA AAG TTG CAA GAA CAA CAA AGC GAT TTA GAA CAA GAG AGA CGT GCT AAA
leu ala lys glu lys leu gln glu gln gln ser asp leu glu gln glu arg arg ala lys
721 /  241                           751 /  251
GAA AAG TTG CAA GAA CAA CAA AGC GAT TTA GAA CAA GAG AGA CGT GCT AAA GAA AAG TTG
glu lys leu gln glu gln gln ser asp leu glu gln glu arg arg ala lys glu lys leu
```

FIGURE 7B

```
781 /  261
CAA GAA CAA AGC GAT TTA GAA CAA GAG AGA CTT GCT AAA GAA AAG TTA CAA GAG CAG
gln glu gln ser asp leu glu gln glu arg leu ala lys glu lys leu gln glu gln
841 /  281                   811 /  271
CAA AGC GAT TTA GAA CAA GAT CAA GAT CTT GCT AAA GAA AAG TTG CAA CAA CAA AGC GAT
gln ser asp leu glu gln asp arg leu ala lys glu lys leu gln gln gln ser asp
901 /  301                   871 /  291
TTA GAA CAA GAG AGA CGT GCT AAA GAA AGG TTG CAA GAA CAA CAA AGC GAT TTA
leu glu gln glu arg arg ala lys glu arg leu gln glu gln gln ser asp leu
                             931 /  311
```

FIGURE 7C

NUCLEOTIDE SEQUENCE OF THE LSA GENE
3' END (CODING 3' END, REPETITIVE)

```
1    CAAGAACAACAAAGCGATCTAGAACAAGAGAGACGT
37   GCTAAAGAAAAGTTGCAAGAACAACAAAGCGATTTAGAACAAGATAGACTT
88   GCTAAAGAAAAGTTACAAGAGCAGCAAAGCGATTTAGAACAAGAGAGACTT
139  GCTAAGAAAAGTTGCAAGAACAACAAAGCGATCTAGAACAAGAGAGACGT
190  GCTAAAGAAAAGTTGCAAGAACAACAAAGCGATTTAGAACAAGAGAGACGT
241  GCTAAAGAAAAGTTGCAAGAACAACAAAGCGATTTAGAACAAGATAGACTT
292  GCTAAAGAAAAGTTACAAGAGCAGCAAAGCGATTTAGAACAAGAGAGACGT
343  GCTAAAGAAAAGTTGCAAGAACAACAAAGCGATTTAGAACAAGAGAGACGT
394  GCTAAGAAAAGTTGCAAGAACAACAAAGCGATTTAGAACAAGAGAGACTT
445  GCTAAAGAAAAGTTGCAAGAACAACAAAGCGATTTAGAACAAGAGAGACGT
496  GCTAAAGAAAAGTTGCAAGAACAACAAAGCGATTTAGAACAAGAGAGACGT
547  GCTAAGAAAAGTTGCAAGAACAACAAAGCGATTTAGAACAAGAGAGACGT
598  GCTAAAGAAAAGTTGCAAGAGCAGCAAAGAGATTTAGAACAA
```

(CODING 3' END, UNIQUE)

```
640  AGGAAGGCTGATACGAAAAAAAATTTAGAAAGAAAAAAGGAACATGGAGAT
691  ATATTAGCAGAGGATTTATATGGTCGTTTAGAAATACCAGCTATAGAACTT
742  CCATCAGAAAATGAACGTGGATATTATATACCACATCAATCTTCTTTACCT
793  CAGGACAACAGAGGGAATAGTAGAGATTCCAAGGAAATATCTATAATAGAA
844  AAAACAAATAGAGAATCTATTACAACAAATGTTGAAGGACGAAGGGATATA
895  CATAAAGGACATCTTGAAGAAAGAAAGATGGTTCAATAAAACCAGAACAA
946  AAAGAAGATAAATCTGCTGACATACAAAATCATACATTAGAGACAGTAAAT
997  ATTTCTGATGTTAATGATTTTCAAATAAGTAAGTATGAGGATGAAATAAGT
1048 GCTGAATATGACGATTCATTAATAGATGAAGAAGAAGATGATGAAGACT
1099 TAGACGAATTTAAGCCTATTGTGCAATATGACAATTTCCAAGATGAAGAAA
1150 ACATAGGAATTTATAAAGAACTAGAAGATTTGATAGAGAAAAATGAAAATT
1201 TAGATGATTTAGATGAAGGAATAGAAAAATCATCAGAAGAATTATCTGAAG
1252 AAAAAATAAAAAAAGGAAAGAAATATGAAAAAACAAAGGATAATAATTTTA
1303 AACCAAATGATAAAGTTTGTATGATGAGCATATTAAAAAATATAAAAATG
1354 ATAAGCAGGTTAATAAGGAAAAGGAAAAATTCATAAAATCATTGTTTCATA
1405 TATTTGACGGAGACAATGAAATTTTACAGATCGTGGATGAGTTATCTGAAG
1456 ATATAACTAAATATTTTATGAAACTA TAA (stop)
```

(NON-CODING 3' END)

```
1485 AAGGTTATATATTT 1498
```

FIGURE 8

LSA.3'.ALL -> 1-phase Translation

DNA sequence 1496 b.p.    CAAGAACAACAA ... GGTTATATATTT    linear

```
1  /   1
CAA GAA CAA AGC GAT CTA GAA CAA GAG AGA CGT GCT AAA GAA AAG TTG CAA GAA CAA
gln glu gln ser asp leu glu gln glu arg arg ala lys glu lys leu gln glu gln
                        31 /  11
61 /  21
CAA AGC GAT TTA GAA CAA GAT AGA CTT GCT AAA GAA AAG TTA CAA CAA GAG CAA AGC GAT
gln ser asp leu glu gln asp arg leu ala lys glu lys leu gln gln glu gln ser asp
                        91 /  31
121 /  41
TTA GAA CAA GAG AGA CTT GCT AAA GAA AAG TTG CAA GAA CAA CAA AGC GAT CTA GAA CAA
leu glu gln glu arg leu ala lys glu lys leu gln glu gln gln ser asp leu glu gln
                        151 /  51
181 /  61
GAG AGA CGT GCT AAA GAA AAG TTG CAA GAA CAA CAA AGC GAT TTA GAA CAA CAA GAG AGA CGT
glu arg arg ala lys glu lys leu gln glu gln gln ser asp leu glu gln gln glu arg arg
                        211 /  71
241 /  81
GCT AAA GAA AAG TTG CAA GAA CAA CAA AGC GAT AGA CTT GCT AAA GAA
ala lys glu lys leu gln glu gln gln ser asp arg leu ala lys glu
                        271 /  91
301 / 101
AAG TTA CAA GAG CAG CAA GAC GAT TTA GAA CAA GAA AGA CGT GCT AAA GAA AAG TTG CAA
lys leu gln glu gln gln ser asp leu glu gln glu arg arg ala lys glu lys leu gln
                        331 / 111
```

FIGURE 9A

```
361 /   121
GAA CAA AGC GAT TTA CAA AGC GAT TTA CAA AGA CGT GCT AAA GAA AAG TTG CAA GAA CAA CAA
glu gln ser asp leu gln ser asp leu gln arg arg ala lys glu lys leu gln glu gln gln
421 /   141
AGC GAT TTA GAA CAA GAG CAA CTT GCT AAA GAA AAG TTG CAA GAA CAA CAA AGC GAT TTA
ser asp leu glu gln glu gln leu ala lys glu lys leu gln glu gln gln ser asp leu
481 /   161
GAA CAA GAG AGA CGT GCT AAA GAA AAG TTG CAA GAA CAA CAA AGC GAT TTA GAA CAA GAG
glu gln glu arg arg ala lys glu lys leu gln glu gln gln ser asp leu glu gln glu
541 /181
AGA CGT GCT AAA GAA AAG TTG CAA GAA CAA CAA GAG TTA GAA CAA GAG AGA CGT GCT
arg arg ala lys glu lys leu gln glu gln gln glu leu glu gln glu arg arg ala
601 /   201
AAA GAA AAG TTG CAA GAG CAG CAA GAT TTA GAA CAA AGG AAG GCT GAT ACG AAA AAA
lys glu lys leu gln glu gln gln asp leu glu gln arg lys ala asp thr lys lys
661 /   221
AAT TTA GAA AGA AAA AAG GAA CAT GGA GAT ATA TTA GCA GAG GAT TTA TAT GGT CGT TTA
asn leu glu arg lys lys glu his gly asp ile leu ala glu asp leu tyr gly arg leu
721 /   241
GAA ATA CCA GCT ATA GAA CTT CCA TCA GAA AAT GAA CGT GGA TAT TAT ATA CCA CAT CAA
glu ile pro ala ile glu leu pro ser glu asn glu arg gly tyr tyr ile pro his gln
781 /   261
TCT TCT TTA CCT CAG GAC AAC AGT AGA GAT TCC AAG GAA ATA TCT ATA ATA
ser ser leu pro gln asp asn ser arg asp ser lys glu ile ser ile ile
```

FIGURE 9B

```
841 /   281
GAA AAA ACA AAT AGA GAA ACA ACA AAT GTT GAA GGA CGA AGG GAT ATA CAT AAA
glu lys thr asn arg glu thr thr asn val glu gly arg arg asp ile his lys
901 /   301
GGA CAT CTT GAA GAA AAG GAT TCT ATT GGT TCA ATA AAA CAA GAA AAA GAT AAA TCT
gly his leu glu glu lys asp ser ile gly ser ile lys pro gln lys asp lys ser
961 /   321
GCT GAC ATA CAA AAT CAT GAG ACA TTA AAT ATT TCT GAT GTT AAT GAT TTT CAA
ala asp ile gln asn his glu thr leu asn ile ser asp val asn asp phe gln
1021 /   341
ATA AGT AAG TAT GAG GAT GAT AGT GCT GAA TAT GAC GAT TCA TTA ATA GAT GAA GAA
ile ser lys tyr glu asp asp ser ala glu tyr asp asp ser leu ile asp glu glu
1081 /   361
GAA GAT GAT GAA GAC TTA GAA TTT AAG CCT ATT GTG CAA TAT GAC AAT TTC CAA GAT
glu asp asp glu asp leu glu phe lys pro ile val gln tyr asp asn phe gln asp
1141 /   381
GAA GAA AAC ATA GGA ATT TAT AAA GAA CTA GAG AAA AAT GAA AAT TTA
glu glu asn ile gly ile gly tyr lys glu leu glu lys asn glu asn leu
1201 /   401
GAT GAT TTA GAT GAA GGA ATA GAA TCA TCA GAA GAA TTA TCT GAA GAA AAA ATA AAA
asp asp leu asp glu gly ile glu ser ser glu glu leu ser glu glu lys ile lys
```

FIGURE 9C

```
1261  /    421                        1291  /    431
AAA GGA AAG AAA TAT GAA AAA ACA AAG GAT AAT AAT TTT AAA CCA AAT GAT AAA AGT TTG
lys gly lys lys tyr glu lys thr lys asp asn asn phe lys pro asn asp lys ser leu
1321  /    441                        1351  /    451
TAT GAT GAG CAT ATT AAA AAA TAT AAA AAT GAT AAG CAG GTT AAT AAG GAA AAG GAA AAA
tyr asp glu his ile lys lys tyr lys asn asp lys gln val asn lys glu lys glu lys
1381  /    461                        1411  /    471
TTC ATA AAA TCA TTG TTT CAT ATA TTT GAC GGA GAC AAT GAA ATT TTA CAG ATC GTG GAT
phe ile lys ser leu phe his ile phe asp gly asp asn glu ile leu gln ile val asp
1441  /    481                        1471  /    491
GAG TTA TCT GAA GAT ATA ACT AAA TAT TTT ATG AAA CTA TAA AAG GTT ATA TAT
glu leu ser glu asp ile thr lys tyr phe met lys leu OCH lys val ile tyr
```

FIGURE 9D

```
LSN.3'STOP ->   1-phase Translation

DNA sequence   1482 b.p.   CAAGAACAACAA ... ATGAAACTATAA   linear

1   /   1                                        31  /  11
CAA GAA CAA CAA AGC GAT CTA GAA CAA GAG AGA CGT GCT AAA GAA AAG TTG CAA GAA GAA
gln glu gln gln ser asp leu glu gln glu arg arg ala lys glu lys leu gln glu glu
61  /  21                                       91  /  31
CAA AGC GAT TTA GAA CAA GAT AGA CTT GCT AAA GAA AAG TTA CAA GAG CAG CAA AGC GAT
gln ser asp leu glu gln asp arg leu ala lys glu lys leu gln glu gln gln ser asp
121 /  41                                       151 /  51
TTA GAA CAA GAG AGA CTT GCT AAA GAA AAG TTG CAA GAA CAA CAA AGC GAT CTA GAA CAA
leu glu gln glu arg leu ala lys glu lys leu gln glu gln gln ser asp leu glu gln
181 /  61                                       211 /  71
GAG AGA CGT GCT AAA GAA AAG TTG CAA GAA CAA CAA AGC GAT TTA GAA CAA GAG AGA CGT
glu arg arg ala lys glu lys leu gln glu gln gln ser asp leu glu gln glu arg arg
241 /  81                                       271 /  91
GCT AAA GAA AAG TTG CAA GAA CAA CAA GAT TTA GAA CAA GAT AGA CTT GCT AAA GAA
ala lys glu lys leu gln glu gln gln asp leu glu gln asp arg leu ala lys glu
301 / 101                                       331 / 111
AAG TTA CAA GAG CAG CAA AGC GAT TTA GAA CAA GAG AGA CGT GCT AAA GAA AAG TTG CAA
lys leu gln glu gln gln ser asp leu glu gln glu arg arg ala lys glu lys leu gln
```

FIGURE 10A

```
361                         391                             /131
GAA CAA AGC GAT TTA GAA CAA CAA AGA CGT GCT AAA GAA AAG TTG CAA GAA CAA CAA
glu gln ser asp leu glu gln gln arg arg ala lys glu lys leu gln glu gln gln
421                         /141                            /151
AGC GAT TTA GAA CAA GAG CTT AGA CGT GCT AAA GAA AAG TTG CAA GAA CAA AGC GAT TTA
ser asp leu glu gln glu leu arg arg ala lys glu lys leu gln glu gln ser asp leu
481                         /161                            /171
GAA CAA GAG AGA CGT GCT AAA GAA AAG TTG CAA GAA CAA CAA AGC GAT TTA GAA CAA GAG
glu gln glu arg arg ala lys glu lys leu gln glu gln gln ser asp leu glu gln glu
541                         /181                            /191
AGA CGT GCT AAA GAA AAG TTG CAA GAA CAA CAA AGC GAT TTA GAA CAA GAG AGA CGT GCT
arg arg ala lys glu lys leu gln glu gln gln ser asp leu glu gln glu arg arg ala
601                         /201                            /211
AAA GAA AAG TTG CAA GAG CAG CAA CAA CAA GAT TTA GAA GAT TTA GCA GAG GAT TTA TAT TAT ATA CCA CAT CAA
lys glu lys leu gln glu gln gln gln gln asp leu glu asp leu ala glu asp leu tyr tyr ile pro his gln
661                         /221                            /231
AAG TTG CAA GAG CAG CAG CAG GAT CAG CAG GAT GGA CAT CAT CAA AGG AAG GCT GAT ACG AAA
lys leu gln glu gln gln gln asp gln gln asp gly his his gln arg lys ala asp thr lys
721                         /251
AAT TTA GAA AGA AAA AAG TTG AAA GAA CAT CAT CAA AGG AAG GCT GAT ACG AAA
asn leu glu arg lys lys leu lys glu his his gln arg lys ala asp thr lys
741
GAA ATA CCA GCT ATA GAA CTT CCA TCA GAA AAT GAA CGT GGA TAT TAT ATA CCA CAT CAA
glu ile pro ala ile glu leu pro ser glu asn glu arg gly tyr tyr ile pro his gln
781                         /271
TCT TCT TTA CCT CAG GAC AAC AGA GGG AAT AGT AGA GAT TCC AAG GAA ATG TCT ATA ATA
ser ser leu pro gln asp asn arg gly asn ser arg asp ser lys glu met ser ile ile
```

FIGURE 10B

```
841  /   281
GAA AAA ACA AAT AGA GAA TCT ATT ACA ACA AAT GTT GAA GGA CGA GAT ATA CAT AAA
glu lys thr asn arg glu ser ile thr thr asn val glu gly arg asp ile his lys
901  /   291
GGA CAT CTT GAA GAA AAG GAT CTA GAT AAA GAT GGT TCA ATA AAA CAA GAA GAT AAA TCT
gly his leu glu glu lys asp lys asp gly ser ile lys pro glu lys asp lys ser
961  /   321
GCT GAC ATA CAA AAT CAT CTA GAG ACA GTA AAT ATT TCT GAT GTT AAT GAT TTT CAA
ala asp ile gln asn his thr leu glu thr val asn ile ser asp val asn asp phe gln
1021 /   351
ATA AGT AAG TAT GAG GAT AGT GCT GAA ATA AGT GCT GAA TAT GAC TAT GAC TCA TTA ATA GAT GAA GAA
ile ser lys tyr glu asp ser ala glu ile ser ala glu tyr asp tyr asp ser leu ile asp glu glu
1081 /   371
GAA GAT GAT GAA GAC TTA GAC GAC TTA GAT GAG GAA TTT AAG CCT ATT GTG CAA TAT GAC AAT TTC CAA GAT
glu asp asp glu asp leu asp glu asp leu asp glu glu phe lys pro ile val gln tyr asp asn phe gln asp
1141 /   391
GAA GAA AAC ATA GGA ATT GGG ATC GGA ATT GGA ATT GAA GAT TTG ATA GAG AAA AAT GAA AAT TTA
glu glu asn ile gly ile gly ile gly ile glu asp leu ile glu lys asn glu asn leu
1201 /   411
GAT GAT TTA GAT GAA GAA GGA ATA GAA AAA TCA TCA GAA GAA TTA TCT GAA GAA AAA ATA AAA
asp asp leu asp glu glu gly ile glu lys ser ser glu glu leu ser glu glu lys ile lys
1261 /   431
AAA GGA AAG AAA TAT GAA ACA AAA ACA AAG GAT AAT AAT TTT AAA CCA AAT GAT AAA AGT TTG
lys gly lys lys tyr glu thr lys thr lys asp asn asn phe lys pro asn asp lys ser leu
```

FIGURE 10C

```
1321                              1351/451
TAT GAT GAG CAT ATT AAA AAA TAT AAA AAT GAT AAG CAG GTT AAT AAG GAA AAG GAA AAA
tyr asp glu his ile lys lys tyr lys asn asp lys gln val asn lys glu lys glu lys
1381/461                          1411/471
TTC ATA AAA TCA TTG TTT CAT ATA TTT GAC GGA GAC AAT GAA ATT TTA CAG ATC GTG GAT
phe ile lys ser leu phe his ile phe asp gly asp asn glu ile leu gln ile val asp
1441/481                          1471/491
GAG TTA TCT GAA GAT ATA ACT AAA TAT TTT ATG AAA CTA TAA AAG GTT ATA TAT
glu leu ser glu asp ile thr lys tyr phe met lys leu OCH lys val ile tyr
```

FIGURE 10D

PEPTIDE SEQUENCES SPECIFIC FOR THE HEPATIC STAGES OF P. FALCIPARUM BEARING EPITOPES CAPABLE OF STIMULATING THE T LYMPHOCYTES

CROSS-REFERENCE TO RELATED APPLICATIONS

This application is a divisional of application Ser. No. 09/837,344, filed on Apr. 19, 2001, now U.S. Pat. No. 7,087,231, which is a divisional of application Ser. No. 08/462,625 filed on Jun. 5, 1995, which is a divisional of application Ser. No. 08/098,327 filed on Nov. 24, 1993, which is a national stage filing under 35 U.S.C. § 371 of International Application No. PCT/FR92/00104 filed on Feb. 5, 1992, which International Application was not published by the International Bureau in English.

BACKGROUND OF THE INVENTION (1) Field of the Invention

The parasites responsible for malaria in man, including in particular *Plasmodium falciparum* and *Plasmodium vivax* to mention only the principal ones among them, exhibit different morphologies in the human host and express different antigens as a function of their localization in the organism of the infected host. The morphological and antigenic differences shown by these parasites during their life cycle in man makes it possible to define at least four distinct stages of development.

(2) Description of the Prior Art

The very first stage of development of the parasite in man corresponds to the sporozoite form introduced into the blood of the host by bites of insect carriers of the parasite. The second stage corresponds to the passage of the parasite into the liver and to the infection of the hepatic cells in which the parasites develop to form the hepatic schizonts, which burst to release the hepatic merozoites. The third stage is characterized by the infection of the blood erythrocytes by the asexual forms (merozoites) of the parasite; this erythrocytic form of development of the parasite corresponds to the pathogenic phase of the disease. The fourth stage corresponds to the formation of the sexual forms (or gametocytes) which will become the extracellular gametes in the mosquito.

It is known that very many studies have been undertaken in order to isolate from the strains of parasites infective for a human host polypeptide fractions to provide for the needs of the in vitro diagnosis of malaria by detection of the corresponding antibodies, on the one hand, and to attempt to vaccinate against malaria, on the other.

For example, libraries of cloned cDNAs derived from the sporozoites of *Plasmodium falciparum* have been established by ENEA et al. (1984) Science, vol. 225, 628-630. It was recognized that these libraries included clones capable of expressing immunogenic polypeptides containing repetitive units of 4 amino acids specific for the circumsporozoite antigen (of *P. falciparum*).

However, little work has been done on the hepatic forms of the parasites responsible for malaria. The morphology of the hepatic forms was described for the first time in 1948 on biopsies taken from infected human volunteers (Trans. Roy. Soc. Trop. Med. Hyg., 41, 785 (1948). It was possible to describe an antigen specific for the hepatic stage of *P. falciparum* in the liver of South American monkeys insensitive to the blood forms of the parasite, but in which the hepatic forms can develop (An. J Trop. Med. Hyg., 33 (3) 336-341 (1984).

The detection of the localization of the liver-specific antigens (designated hereafter by LS antigens for "Liver Stage" antigens) was carried out by immunofluorescence throughout the maturation steps of the schizont. They are localized at the periphery of the parasite 5 to 40 microns in size; subsequently they are distributed between the cytomers or packets of merozoites, when the schizonts attain between 50 and 100 microns. They are different from the surface antigens of the sporozoites and the antigens shared by the schizonts of the blood and the liver which give an internal immunoflucrescence image of the parasite.

Although it is now possible to culture hepatic forms of *P. falciparum* in human hepatocytes (Science, 227 440 (1985)), the low numbers of mature forms of the parasite obtained by the in vitro and in vivo culture methods do not allow the biochemical analysis of the antigen produced at the hepatic stage.

It has also been observed that the individuals suffering from malaria possess a very high level of antibodies directed against the LSA. The LS antigens seem to be very potent immunogens, among the most potent of all of the antigens synthesized at the various stages of development of the parasite.

One of the objectives of the present invention is precisely to provide novel compositions for the vaccination of humans against the malaria caused by *P. falciparum*.

The objective of the invention is also the in vitro diagnosis of the infection of an individual by *P. falciparum* under more sensitive conditions than present methods allow.

A molecule expressed specifically during the hepatic phase has been identified by screening a library of genomic DNA cloned in an expression vector with polyclonal sera (GUERIN-MARCHAND, C. et al.; Nature, 329, 164-167 (1987)). This molecule represents a part of an antigen called LSA (Liver Stage Specific antigen), and is constituted of repetitive motifs of 17 amino acids and seems to be very immunogenic under the natural conditions of exposure to the disease.

These repetitive motifs (SEQ ID NO: 1) of 17 amine acids are represented by the formula:

Leu-Ala-Lys-Glu-Lys-Leu-Gln-X-Gln-Gln-Ser-Asp-Leu-Glu-Gln-Glu-Arg in which X is Glu or Gly.

The subject of the invention is peptide sequences specific for the hepatic stages of *P. falciparum* which bear epitopes capable of stimulating the T lymphocytes (in particular the cytotoxic lymphocytes).

The invention relates more particularly to molecules or to peptide or polypeptide compositions characterized by the presence in their structure of one or more peptide sequences bearing all or part of one or more T epitope(s) (epitopes implicated in the stimulation of the T lymphocytes) and, optionally, other epitopes, in particular B epitopes (epitopes corresponding to the antibodies produced by B lymphocytes), characteristic of the proteins resulting front the infectious activity of *P. falciparum* in the liver cells.

BRIEF DESCRIPTION OF THE DRAWINGS

Reference will be made in what follows to the Figures in which:

FIG. 1 (SEQ ID NO: 31) presents a recombinant protein of the invention of 316 amino acids, designated hereafter as antigen 536 or protein LSA-R-NR, FIG. 2 (SEQ ID NO: 32) provides the nucleotide sequence of one of the recombinant nucleic acids studied (clone DG536) and which codes for the polypeptide LSA-R-NR, FIG. 3 (SEQ ID NO: 24) presents a polypeptide of the invention of 151 amino acids, designated hereafter as antigen 729S, FIG. 4 (SEQ ID NO: 33) corresponds to the nucleotide sequence of the clone DG729S which codes for the polypeptide of FIG. 3 (EcoRI linkers in bold type), FIG. 5 presents the polypeptide sequences (SEQ ID NOS: 23 and 26-28) of the antigens LSA-TER, 729S-NRI, 729S-NRII, 729S-Rep, FIG. 6 (SEQ ID NO: 34) presents the 5' end of the nucleotide sequence of the LSA gene, FIGS. 7A-7C (SEQ ID NOS: 35-37) presents the coding sequence of the 5' end of the LSA gene and the corresponding polypeptide sequence, FIG. 8 (SEQ ID NO: 38) describes the 3' end of the LSA gene, FIGS. 9A-9D (SEQ ID NOS: 39-42) gives the sequence of the 3' end of the LSA gene as well as the corresponding polypeptide sequence, FIGS. 10A-10D (SEQ ID NOS: 43-46) repeats the sequences given in FIGS. 9A-9D, up to the termination codon stop and the terminal amino acid.

DETAILED DESCRIPTION OF THE INVENTION

Thus, the present invention relates to any molecule or polypeptide composition bearing at least one peptide sequence bearing all or part of one or more epitopes characteristic of a protein produced in the hepatocytes infected by $P. falciparum$, and more particularly bearing all or part of one or more T epitope(s) of the proteins produced at the hepatic stage of $P. falciparum$, characterized in that this peptide sequence is represented by all or part of the amino acid sequence shown in FIGS. 9A-9D or FIGS. 10A-10D, and corresponds to the 3' end of the LSA gene.

More particularly, the subject of the invention is any molecule or polypeptide composition bearing at least one peptide sequence bearing all or part of one or more epitopes characteristic of a protein produced in the hepatocytes infected by $P. falciparum$, and more particularly bearing all or part of one or more T epitope(s) of the proteins produced at the hepatic stage of $P. falciparum$. characterized in that this peptide sequence is represented by all or part of the sequence of the last 279 amino acids shown in FIGS. 10A-10D, this amino acid sequence being optionally preceded by all or part of one or more of the sequences of 17 amino acids (SEQ ID NOS: 2-18) of formula:

$X_1$DLEQ$X_2$R$X_3$AKEKLQ$X_4$QQ,

Q$X_1$DLEQ$X_2$R$X_3$AKEKLQ$X_4$Q,

QQ$X_1$DLEQ$X_2$R$X_3$AKEKLQ$X_4$, $X_4$QQ$X_1$DLEQ$X_2$R$X_3$AKEKLQ,

Q$X_4$QQ$X_1$DLEQ$X_2$R$X_3$AKEKL,

LQ$X_4$QQ$X_1$DLEQ$X_2$R$X_3$AKEK,

KLQ$X_4$QQ$X_1$DLEQ$X_2$R$X_3$AKE,

EKLQ$X_4$QQ$X_1$DLEQ$X_2$R$X_3$AK,

KEKLQ$X_4$QQ$X_1$DLEQ$X_2$R$X_3$A,

AKEKLQ$X_4$QQ$X_1$DLEQ$X_2$R$X_3$A, $X_3$AKEKLQ$X_4$QQ$X_1$DLEQ$X_2$R,

R$X_3$AKEKLQ$X_4$QQ$X_1$DLEQ$X_2$, $X_2$R$X_3$AKEKLQ$X_4$QQ$X_1$DLEQ,

Q$X_2$R$X_3$AKEKLQ$X_4$QQ$X_1$DLE,

EQ$X_2$R$X_3$AKEKLQ$X_4$QQ$X_1$DL,

LEQ$X_2$R$X_3$AKEKLQ$X_4$QQ$X_1$D,

DLEQ$X_2$R$X_3$AKEKLQ$X_4$QQ$X_1$, in which $X_1$ is "Ser" or "Arg"

$X_2$ is "Glu" or "Asp"

$X_3$ is "Arg" or "Leu"

$X_4$ is "Glu" or "Gly".

Consequently, the invention relates more particularly to any molecule or polypeptide composition bearing at least one peptide sequence bearing all or part of one or more epitopes characteristic of a protein produced in the hepatocytes infected by $P. falciparum$, and more particularly bearing all or part of one or more T epitope(s) of the proteins produced at the hepatic stage of $P. falciparum$, characterized in that this peptide sequence is represented by all or part of the following amino acid sequence (SEQ ID NO: 19):

RKADTKKNLERKKEHGDILAEDLYGRLEIPAIELPS

ENERGYYIPHQSSLPQDNRGNSRDSKEISIIEKTNR

ESITTNVEGRRDIHKGHLEEKDGSIKPEQKEDKS this amino acid sequence being optionally preceded by all or part of one or more sequences of 17 amino acids (SEQ ID NOS: 2-18) of formula:

$X_1$DLEQ$X_2$R$X_3$AKEKLQ$X_4$QQ,

Q$X_1$DLEQ$X_2$R$X_3$AKEKLQ$X_4$Q,

QQ$X_1$DLEQ$X_2$R$X_3$AKEKLQ$X_4$, $X_4$QQ$X_1$DLEQ$X_2$R$X_3$AKEKLQ,

Q$X_4$QQ$X_1$DLEQ$X_2$R$X_3$AKEKL,

LQ$X_4$QQ$X_1$DLEQ$X_2$R$X_3$AKEK,

KLQ$X_4$QQ$X_1$DLEQ$X_2$R$X_3$AKE,

EKLQ$X_4$QQ$X_1$DLEQ$X_2$R$X_3$AK,

KEKLQ$X_4$QQ$X_1$DLEQ$X_2$R$X_3$A,

AKEKLQ$X_4$QQ$X_1$DLEQ$X_2$R$X_3$, $X_3$AKEKLQ$X_4$QQ$X_1$DLEQ$X_2$R,

R$X_3$AKEKLQ$X_4$QQ$X_1$DLEQ2, $X_2$R$X_3$AKEKLQ$X_4$QQ$X_1$DLEQ,

Q$X_2$R$X_3$AKEKLQ$X_4$QQ$X_1$DLE,

EQX₂RX₃AKEKLQX₄QQX₁DL,

LEQX₂RX₃AKEKLQX₄QQX₁D,

DLEQX₂RX₃AKEKLQX₄QQX₁, in which:

X₁ is "Ser" or "Arg"

X₂ is "Glu" or "Asp"

X₃ is "Arg" or "Leu"

X₄ is "Glu" or "Gly".

Thus the present invention relates in particular to the peptide sequence shown in FIG. 1. This sequence is constituted of 316 amino acids. At the 5' end 209 amino acids are found organized in repeats of 17 amino acids corresponding to the formulae indicated above. At the 3' end, repeats totalling 107 amino acids are found.

The invention relates more particularly to any polypeptide characterized by all or part of the following amino acid sequence (SEQ ID NO: 20):

```
LQEQQRDLEQRKADTKKNLERKKEHGDILAEDLYGRLEIPAIELPSENERGYY

IPHQSSLPQDNRGNSRDSKEISIIEKTNRESITTNVEGRRDIHKGHLEEKKDG

SIKPEQKEDKS
```

A preferred polypeptide of the invention is represented by all or part of the following amino acid sequence (SEQ ID NO: 21):

```
DTKKNLERKKEHGDILAEDLYGRLEIP
```

(this polypeptide being designated hereafter by the expression LSA-NR (LSA-non-repeated), or also by any sequence derived from the preceding sequence and modified by the substitution of maximally 40% of the amino acids while retaining its physiological activity such as the induction of a response of the T lyphocytes, in particular the cytotoxic T lymphocytes.

Another particularly preferred polypeptide of the invention is characterized by all or part of the following amino acid sequence (SEQ ID NO: 22):

```
ERRAKEKLQEQQRDLEQRKADTKK
```

(this polypeptide being designated hereafter by the expression LSA-J, or LSA-junction, since it overlaps the repetitive part and the non-repetitive part of the molecule shown in FIG. 1).

Another preferred peptide, designated LSA-TER, is the following (SEQ ID NO: 23):

```
NSRDSKEISIIEKTNRESITTNVEGRRDIHK
```

These last three polypeptides are more particularly useful on account of the amphipaticity which characterizes them, and because of their three-dimensional conformation according to the predictions made by the procedure of Chou and Fassmann.

The subject of the invention is also any molecule or polypeptide composition bearing at least one peptide sequence bearing all or part of one or more epitope(s) characteristic of a protein produced at the sporozoite, hepatic and blood (erythrocytic) stages of *P. falciparum*, and more particularly bearing one or more T epitopes, characterized in that this peptide sequence is represented by all or part of the following amino acid sequence (SEQ ID NO: 24):

```
RDELFNELLNSVDVNGEVKENILEESQVNDDIFNSLVKSVQQEQQHNVEEKVE

ESVEENDEESVEENVEENVEENDDGSVASSVEESIASSVDESIDSSIEENVAP

TVEEIVAPTVEEIVAPSVVEKCAPSVEESVAPSVEESVAEMLKER
``` shown in FIG. 3 and designated hereafter as the polypeptide 729S.

More particularly, the subject of the invention is the amino acid sequence derived from the preceding sequence and characterized by all or part of the following amino acid sequence (SEQ ID NO: 25):

```
RDELFNELLNSVDVNGEVKENILEESQVNDDIFNSLVKSVQQEQQHN
```

According to another advantageous embodiment of the invention, sequences of interest derived from the amino acid sequence of the polypeptide 729S are the following (SEQ ID NOS: 26-28):

```
DELFNELLNSVDVNGEVKENILEESQ,

LEESQVNDDIFSNSLVKSVQQEQQHNV,

VEKCAPSVEESVAPSVEESVAEMLKER.
```

These sequences are designated 729S-NRI, 729S-NRTI, 729S-Rep, respectively.

The subject of the invention is also any molecule or polypeptide composition comprising at least one peptide sequence bearing all or part of one or more epitopes characteristic of a protein produced in the hepatocytes infected by *P. falciparum*, characterized in that this peptide sequence is represented by all or part of the amino acid sequence shown in FIGS. 7A-7C.

Consequently, the subject of the invention is more particularly any molecule or polypeptide composition comprising at least one peptide sequence bearing all or part of one or more epitopes characteristic of a protein produced in the hepatocytes infected by *P. falciparum*, and bearing more particularly all or part of one or more T epitope(s) of the proteins produced at the hepatic stage of *P. falciparum*, characterized in that this peptide sequence is represented by all or part of the sequence of the first 153 amino acids shown in FIGS. 7A-7C, this amino acid sequence being optionally followed by all or part of one or more sequences of 17 amino acids (SEQ ID NOS: 2-18) of formula:

$X_1DLEQX_2RX_3AKEKLQX_4QQ$, $QX_1 DLEQX_2RX_3AKEKLQX_4Q$, $QQX_1DLEQX_2RX_3AKEKLQX_4$, $X_4QQX_1DLEQX_2RX_3AKEKLQ$, $QX_4QQX_1DLEQX_2RX_3AKEKL$, $LQX_4QQX_1DLEQX_2RX_3AKEK$, $KLQX_4QQX_1DLEQX_2RX_3AKE$, $EKLQX4QQX_1DLEQX_2RX_3AK$, $KEKLQX_4QQX_1DLEQX_2RX_3A$, $AKEKLQX_4QQX_1DLEQX_2RX_3$, $X_3AKEKLQX_4QQX_1DLEQX_2R$, $RX_3AKEKLQX_4QQX_1DLEQX_2$, $X_2RX_3AKEKLQX_4QQX_1DLEQ$, $QX_2RX_3AKEKLQX_4QQX_1DLE$, $EQX_2RX_3AKEKLQX_4QQX_1DL$, $LEQX_2RX_3AKEKLQX_4QQX_1D$, $DLEQX_2RX_3AKEKLQX_4QQX_1$, in which $X_1$ is "Ser" or "Arg"

$X_2$ is "Glu" or "Asp"

$X_3$ is "Arg" or "Leu"

$X_4$ is "Glu" or "Gly".

The invention also relates to any molecule or polypeptide composition comprising at least one peptide sequence bearing all or part of one or more epitopes characteristic of a protein produced in the hepatocytes infected by *P. falciparum*, and bearing more particularly all or part of one or more T epitope(s) of the proteins produced at the hepatic stage of *P. falciparum*, characterized in that this peptide sequence comprises successively:

all or part of the sequence of the first 153 amino acids shown in FIGS. 7A-7C, optionally, all or part of one or more of the sequences of 17 amino acids (SEQ ID NOS: 2-18) of formula:

$X_1DLEQX_2RX_3AKEKLQX_4QQ$, $QX_1DLEQX_2RX_3AKEKLQX_4Q$, $QQX_1DLEQX_2RX_3AKEKLQX_4$, $X_4QQX_1DLEQX_2RX_3AKEKLQ$, $QX_4QQX_1DLEQX_2RX_3AKEKL$, $LQX_4QQX_1DLEQX_2RX_3AKEK$, $KLQX_4QQX_1DLEQX_2RX_3AKE$, $EKLQX_4QQX_1DLEQX_2RX_3AK$, $KEKLQX_4QQX_1DLEQX_2RX_3A$, $AKEKLQX_4QQX_1DLEQX_2RX_3$, $X_3AKEKLQX_4QQX_1DLEQX_2R$, $RX_3AKEKLQX_4QQX_1DLEQX_2$, $X_2RX_3AKEKLQX_4QQX_1DLEQ$, $QX_2RX_3AKEKLQX_4QQX_1DLE$, $EQX_2RX_3AKEKLQX_4QQX_1DL$, $LEQX_2RX_3AKEKLQX_4QQX_1D$, $DLEQX_2RX_3AKEKLQX_4QQX1$, in which:

$X_1$ is "Ser" or "Arg"

$X_2$ is "Glu" or "Asp"

$X_3$ is "Arg" or "Leu"

$X_4$ is "Glu" or "Gly".

and all or part of the last 279 amino acids shown in FIGS. 10A-10D.

The invention also relates to any polypeptide composition constituted by several different peptide sequences which bear all or part of one or more epitope(s) characteristic of a protein produced in the hepatocytes infected by *P. falciparum* as described above.

Generally speaking, by all or part of a peptide sequence of the invention is meant any sequence comprising a least 4 to 5 amine acids up to the maximal number of amino acids of the sequences described above.

It will be obvious that the free reactive functions that some amino acids included in the composition of the molecules according to the invention may possess, in particular the free carboxyl groups borne by the Glu residues or by the C-terminal amino acid, on the one hand, and/or the free groups borne by the N-terminal amino acid or by amino acids within the peptide chain, for example Lys, on the other, may be modified, provided that this modification does not lead to a modification of the antigenic properties, or, according to circumstances, immunogenic properties of the whole molecule. The molecules thus modified are automatically included in the framework of protection given to the invention by the Claims. These carboxyl functions may possibly be acylated or esterified.

Other modifications are also included in the framework of the invention. In particular, the amine or ester functions of the terminal amino acids, or both at once, may themselves be linked to other amino acids. For example, the N-terminal amino acid may be linked to a sequence comprising from one to several amine acids corresponding to a part of the C-terminal region of another peptide conforming to the definition which was given to it above, or vice versa.

It will also be obvious that any peptide sequence derived from the modification by substitution and/or by addition and/or deletion of one or more amine acids of one of the peptide sequences described above is included in the framework of protection given to the invention by the Claims, provided that this modification does net impair the antigenic or immunogenic properties of the polypeptides of the invention, in particular when these immunogenic properties have been reinforced adequately, for example by combination of these polypeptides with a suitable immunological adjuvant (for example, a muramyl peptide) or by coupling to a carrier molecule of higher molecular weight (for example, a serum albumin or a polylysine) or a toxin of the tetanus type or another antigen of *P. falciparum*

More particularly, the invention relates to any peptide sequence derived from the peptide sequences mentioned above, and exhibiting modifications resulting from substitution of maxima 40% of the amino acids while retaining the biological activity of the sequences of the invention, namely in particular the induction of a response of the T lymphocytes, in particular the cytotoxic T lymphocytes.

The invention relates more generally to any molecule characterized by the presence in its structure of one or more peptide sequences which exhibit immunological cross-reactions with the peptide sequences corresponding to the preceding formulae towards antibodies which can be induced by these latter in vivo.

The invention also relates to any sequence of nucleotides which codes for a polypeptide of the invention and, more particularly, sequence of nucleotides corresponding to one of the amino acid sequences of the invention according to the universal genetic code.

The subject of the invention is more particularly the nucleotide sequence constituted by the 951 nucleotides shown in FIG. 2, and which code for the above-mentioned polypeptide of 316 amino acids (also designated hereafter by the recombinant protein LSA-R-NR) shown in FIG. 1.

The invention also relates to the nucleotide sequence shown in FIG. 8, which corresponds to the 3' end of the LSA gene.

The invention also relates to the nucleotide sequences which code for peptide subsequences of the invention. Particular mention should be made of the nucleotide sequences delimited by the nucleotides situated at the positions 630 to 949, 597 to 648 (coding for the peptide LSA-J) or 640 to 717 (coding for the peptide LSA-NR) of FIG. 2.

The invention also relates to all or part of the nucleotide sequence of FIG. 4 which codes for all or part of the peptide sequence 729S shown in FIG. 3.

The subject of the invention is also the nucleotide sequence shown in FIG. 5, which corresponds to the 5' end of the LSA gene.

The invention also relates to any sequence of nucleotides which codes for a polypeptide identical with, or one similar from the point of view of both structure and antigenic properties to, those of the invention, this sequence being capable of hybridizing with all or part of the nucleotide sequence defined by the nucleotides situated at the positions 597 to 949 of FIG. 2, or with all or part of the nucleotide sequence of FIG. 4 or the sequences complementary to these latter, under the following conditions:

pre-treatment (pre-hybridization) of the nitrocellulose filter supporting the nucleic acid fragment to be tested with hybridization buffer (composed of 6 SSC, 5× Denhardt's, 0.5% SDS, 100 µg/l denatured, sonicated salmon sperm DNA) this operation being carried out at 65° C. for 1 hour;

replacement of the hybridization buffer in contact with the support to which the nucleic acid fragment is now bound by hybridization buffer of the same composition and addition of the above-mentioned sequence shown in FIG. 2 (SEQ ID NO: 32) or FIG. 4 (SEQ ID NO: 33) as probe, in particular radioactively labelled, and denatured beforehand;

incubation of the said nucleic acid fragment bound to the support in this incubation buffer with the above-mentioned sequence shown in FIG. 2 (SEQ ID NO: 32) or FIG. 4 (SEQ ID NO: 33) at 65° C. for a period of about 1 hour;

the removal of the buffer containing the probe not bound by two successive washings of 30 minutes each with a buffer solution composed of 2×SSC and 0.5% SDS at 65° C.

It should be recalled that 20×SSC=175.3 g NaCl, 88.2 g trisodium citrate/l, pH 7; Denhardt's 50×=5 g Ficoll 400, 5 g polyvinyl pyrrolidone, 5 g BSA (bovine serum albumin) fraction V/l; SDS is sodium dodecyl sulfate.

The subject of the invention is any recombinant nucleic acid containing at least one nucleotide sequence of the invention inserted M a nucleic acid heterologous with respect to the said nucleotide sequence.

The invention relates more particularly to a recombinant nucleic acid such as that defined above in which the nucleotide sequence of the invention is preceded by a promoter (in particular, an inducible promoter) under the control of which transcription of the said sequence is capable of being carried out and optionally followed by a sequence coding for signals for the termination of transcription.

The invention relates to any recombinant vector, used in particular for cloning a nucleotide sequence of the invention and/or the expression of the polypeptide encoded in this sequence, and characterized in that it contains a recombinant nucleic acid such as that defined above at one of its sites inessential for its replication.

As an example of a vector mentioned above, mention should be made of plasmids, cosmids or phages.

Consequently, the invention relates more particularly to the plasmid DG3536 deposited with the CNCM under the No. I-1027 on 17 Jan. 1991, as well as the plasmid DG729S deposited with the CNCM under the No. I-1028 on 17 Jan. 1991.

The subject of the invention is also a procedure for the preparation of a polypeptide of the invention by transformation of a cell host with the aid of a recombinant vector of the type indicated above, followed by the placing of the thus transformed cell host in culture and the recovery of the polypeptide from the culture medium.

Thus, the invention relates to any cell host transformed by a recombinant vector as defined above and which comprises the regulatory elements which allow the expression of the nucleotide sequence coding for a polypeptide according to the invention.

The subject of the invention is more particularly DNA (or RNA) primers which can be used in the context of the synthesis of nucleotide and/or polypeptide sequences according to the invention by the PCR (Polymerase Chain Reaction) procedure, as described in the American Pat. Nos. 4,683,202 and No.4,683,195 and the European patent application No. 200.362 (PCR=assembly-line amplification of the DNA).

The invention relates to any DNA or RNA primer, characterized in that it is constituted of about 10 to 25 nucleotides identical with the first 10 to 25 nucleotides of the nucleotide sequence which codes for a peptide sequence according to the invention or identical with the last 10 to 25 nucleotides of the said sequence.

The invention also relates to any DNA or RNA primer, characterized in that it is constituted of about 10 to 25 nucleotides complementary to the first 10 to 25 nucleotides of the nucleotide sequence according to the invention or complementary to the last 10 to 25 nucleotides of the said nucleotide sequence.

The subject of the invention is also any DNA or RNA primer, characterized in that it is constituted of about 10 to 25 nucleotides which are capable of hybridizing with the first 10 to 25 nucleotides or with the last 10 to 25 nucleotides of the said nucleotide sequence which codes for a polypeptide of the invention under the conditions of hybridization defined above.

Thus the present invention relates more particularly to a procedure for the preparation of a polypeptide of the invention comprising the following steps:

optionally, the prior amplification according to the PCR procedure of a quantity of the nucleotide sequence which codes for the said polypeptide with the aid of two DNA primers selected such that one of these primers is identical with the first 10 to 25 nucleotides of the nucleotide sequence which codes for the said polypeptide, whereas the other primer is complementary to the last 10 to 25 nucleotides (or hybridizes with these last 10 to 25 nucleotides) of the said nucleotide sequence, or conversely such that one of these primers is identical with the last 10 to 25 nucleotides of the said sequence, whereas the other primer is complementary to the first 10 to 25 nucleotides (or hybridizes with these first 10 to 25 nucleotides) of the said nucleotide sequence, followed by the introduction of the said nucleotide sequences thus amplified into a suitable vector, the placing in culture in a suitable culture medium of a cell host previously transformed by a suitable vector containing a nucleic acid according to the invention containing the nucleotide sequence which codes for the said polypeptide, and the recovery of the polypeptide produced by the said transformed cell host from the above-mentioned culture medium.

As examples of DNA or RNA primers according to the invention, mention should be made of the following sequences (SEQ ID NOS: 29 and 30):

```
3'→5: TTTCGCTAGATCTTGTT & TCTAAATAGAAGAAA.
```

The peptides according to the invention may also be prepared by the standard procedures used in the field of peptide synthesis. Such synthesis may be carried out in homogeneous solution or on a solid phase.

For example, recourse may be had to the synthetic procedure in homogeneous solution described by HOUBEM-WEYL in the monograph entitled "Methoden der Organischen Chemie" (Methods of Organic Chemistry) edited by E. Wunsch, vol. 15-I and II, THIEME, Stuttgart 1974.

This method of synthesis consists of successively condensing the successive aminoacyl residues in the required order, or of condensing aminoacyl residues and fragments previously formed which already contain several amino acids in the correct order, or also of condensing several fragments thus prepared beforehand, it being understood that care will be taken to protect beforehand all of the reactive functions borne by these aminoacyl residues or fragments, with the exception of the amino function of the one and the carboxyl function of the other or vice versa, which are usually required to participate in the formation of the peptide bonds, in particular after activation of the carboxyl function according to the methods well known in peptide synthesis. As a variant, it will also be possible to have recourse to coupling reactions which make use of standard coupling reagents of the carbodiimide type, such as for example 1-ethyl-3- (3-dimethylaminopropyl)-carbodiimide.

When the amino acyl residue used possesses an additional acidic function (in particular in the case of glutamic acid), such functions should be protected for example by t-butyl ester groups.

In the case of stepwise synthesis, the amino acids being added one at a time, the synthesis begins preferably with the condensation of the C-terminal amino acid with the amino acid which corresponds to the neighbouring aminoacyl residue in the desired sequence and so on, one after the other, until the N-terminal amino acid is reached.

According to another preferred procedure of the invention, recourse is had to that described by k. B. MERRIFIELD in the article entitled "Solid phase peptide synthesis" (J. Am. Chem. Soc., 45, 2149-2154).

In order to synthesize a peptide chain according to the MERRIFIELD procedure, recourse is had to a very porous polymeric resin to which the first, C-terminal amine acid of the chain is attached. This amine acid is attached to the resin through the intermediary of its carboxyl group and its amine function is protected, for example by means of the t butoxycarbonyl group.

When the first, C-terminal amino acid has thus been attached to the resin, the protecting group of the amino function is removed by washing the resin with acid.

In the case in which the protecting group of the amine function is the t-butoxycarbonyl group, it may be removed by treatment of the resin with trifluoroacetic acid.

The second amino acid is then coupled to the deprotected amine function of the first C-terminal amino acid to furnish the second aminoacyl residue of the desired sequence, counting from the C-terminus. Preferably, the carboxyl function of this second amino acid is activated for example by means of dicyclohexylcarbodiimide and the amine function is protected, for example by means of t-butoxycarbonyl.

The first part of the desired peptide chain is thus produced, which contains two amino acids and the terminal amino function of which is protected. As previously, the amine function is deprotected and it is then possible to proceed to the attachment of the third aminoacyl residue under conditions analogous to those for the addition of the second, penultimate C-terminal amino acid.

In this way, the amino acids which will constitute the peptide chain are added one after the other to the previously deprotected amine group of the portion of the peptide chain already formed which is attached to the resin.

When the desired peptide chain has been assembled in its entirety, the protecting groups of the different side chains of the amino acids constituting the peptide chain are removed and the peptide is cleaved from the resin, for example with the aid of hydrogen fluoride.

The invention also relates to water-soluble oligomers of the monomeric peptides indicated above.

The oligomerization may cause an increase in the immunogenicity of the monomeric peptides according to the invention. Without such numerical values being considered as limiting, it should nonetheless be mentioned that these oligomers may contain, for example, from 2 to 10 monomeric units.

In order to carry out the oligomerization, recourse may be had to any polymerization procedure commonly used in the field of peptides, this polymerization being conducted until an oligomer or polymer is obtained which contains the required number of monomeric motifs for the acquisition of the desired immunogenicity.

One method of oligomerization or polymerization of the monomer consists in the reaction of the latter with a crosslinking agent such as glutaraldehyde.

It is also possible to have recourse to other methods of oligomerization or coupling, for example to that making use of the successive coupling of monomeric units through the intermediary of their terminal carboxyl and amine functions in the presence of homo- or hetero bifunctional coupling agents.

The invention also relates to the conjugates obtained by covalent coupling of the peptides according to the invention (or the above mentioned oligomers) to carrier molecules (natural or synthetic), physiologically acceptable and non-toxic, through the intermediary of complementary reactive groups borne respectively by the carrier molecule and the peptide. Examples of suitable groups are illustrated in what follows:

As examples of carrier molecules or macromolecular supports forming part of the composition of the conjugates according to the invention, mention should be made of naturally occurring proteins such as tetanus toxoid, ovalbumin, serum albumin, hemocyanins, the PPD of tuberculin (PPD : "Purified Protein Derivative"), etc . . .

Mention should be made, for example, of polylysines or poly (D-L alanine) -poly (L-lysine) as examples of synthetic macromolecular supports.

The literature mentions other types of macromolecular supports which can be used and which usually have a molecular weight higher than 20,000.

In order to synthesize the conjugates according to the invention, recourse may be had to known procedures such as that described by FRANTZ and ROBERTSON in Infect. and Immunity, 33, 193-198 (1981) or that described in Applied and Environmental Microbiology, (October 1981), vol. 42, No. 4, 611-614 by P. E. KAUFFMAN by using the peptide and the appropriate carrier molecule.

In practice, the following compounds, cited in a non-limiting manner, are advantageously used as coupling agents: glutaraldehyde, ethyl chloroformate, water-soluble carbodiimides: N-ethyl-N' (3-dimethylamino-propyl) carbodiimide HCl, diisocyanates, bis-diazobenzidine, di- and tri chloro-s-triazines, cyanogen bromide as well as the coupling agents mentioned in Scand. J. Immunol., (1978), vol. 8, p. 7-23 (AVRAMEAS, TERNYNCK, GUESDON).

It is possible to have recourse to any coupling procedure implicating, on the one hand, one or more reactive functions of the peptide and, on the other, one or more reactive functions of the molecular supports. Advantageously, these are carboxyl and amine functions which can give rise to a coupling reaction in the presence of a coupling agent of the type used in the synthesis of proteins, for example, 1-ethyl-3-(3-dimethylamino-propyl)-carbodiimide, N-hydroxybenzotriazole, etc. . . . It is a possible to have recourse to glutaraldehyde, in particular when it is required to link together amino groups borne by the peptide and the molecular support, respectively.

The nucleic acids of the invention can be prepared either by a chemical procedure or by other procedures.

A suitable method of preparation of the nucleic acids containing a maximum of 200 nucleotides (or 200 bp when double-stranded nucleic acids are concerned) of the invention comprises the following steps:

the synthesis of DNA using the automated beta-cyanoethylphosphoramidite method described in Bio-organic Chemistry 4; 274-325 (1986), the cloning of the nucleic acids thus obtained in a suitable vector and the recovery of the nucleic acid with a suitable probe.

A method of preparation by the chemical route of nucleic acids longer than 200 nucleotides (or 200 bp when double-stranded nucleic acids are concerned) of the invention comprises the following steps.

the assembly of chemically synthesized oligonucleotides, provided at their ends with different restriction sites, the sequences of which are compatible with the amino acid sequence of the natural polypeptide according to the principle described in Proc. Natl. Acad. Sci. USA, 80; 7461-7465, (1983), the cloning of the nucleic acids thus obtained in a suitable vector and the recovery of the desired nucleic acid by means of hybridization with a suitable probe.

The nucleic acids of the invention can a be prepared in the following manner incubation of the genomic DNA isolated front a strain of *P. falciparum* with DNase I, then addition of EDTA and purification by extraction with the mixture phenol/chloroform/isoamyl alcohol (25/24/1), then with ether, treatment of the DNA thus extracted with the EcoRI methylase in the presence of DTT, and purification by extraction as described above, incubation of the DNA thus purified with the 4 deoxynucleoside triphosphates dATP, dCTP, DGTP and dTTP in the presence of T4 DNA polymerase and DNA ligase of *E. coli*, followed by purification according to the method described above, the cloning of the nucleic acids thus obtained in a suitable vector and the recovery of the desired nucleic acid with the aid of a suitable probe.

The nucleotide probes used for the recovery of the desired nucleic acid in the procedures mentioned above are usually composed of 40 to 200 nucleotides of the nucleotide sequence shown in FIG. 2 (selected more particularly front those situated between the positions 597 to 949 shown in FIG. 2) or in FIG. 4 or its complementary sequence, and are capable of hybridizing with the desired nucleic acid under the conditions of hybridization defined above. The synthesis of these probes is carried out according to the automated beta-cyanoethylphosphoramidite method described in Bio-organic Chemistry 4, 274-325 (1986).

The molecules according to the invention possess antigenic properties characteristic of the antigens which bear T epitopes, and optionally B epitopes, and which are either specific for the hepatic stage of the development of *P. faiciparum* or specific for the sporozoite, hepatic and blood stages, simultaneously.

In fact, as will be described more particularly with the aid of examples of molecules according to the invention in the detailed description which follows, the molecules according to the invention which contain all or part of the amino acid sequence comprised between the positions 200 and 316 shown in FIG. 1 (SEQ ID NO: 31), react specifically with the antibodies or the lymphocytes directed against the B and/or T epitopes of the antigens produced at the hepatic stage of *P. falciparum*, but not with the antibodies directed against other antigens produced by *P. falciparum* or against antigens produced by other species of *Plasmodium*.

These molecules according to the invention thus recognize specifically the antibodies produced by the immune system of an individual infected by *P. falciparum* under the influence of the LSA antigen, the strongly immunogenic character of which has already been mentioned.

These molecules according to the invention comprising all or part of the peptide sequence shown in FIG. 3 (SEQ ID NO: 24) are not recognized by the former antibodies which react specifically with all or part of the polypeptide defined by the amino acids situated at the positions 200 to 316 in FIG. 1.

On the other hand, the polypeptides corresponding to all or part of the peptide sequence shown in FIG. 3 (SEQ ID NO: 24) are recognized by antibodies which react specifically with antigens localized on the surface of sporozoites (derived from different strains of *P. falciparum*) as well as with antigens of the hepatic schizonts and the blood schizonts, and finally with the surface of the sporozoites of *P. yoelii* but not of *P. berghei*.

It should also be emphasized that the antibodies which recognize specifically the polypeptides corresponding to all or part of the peptide sequence shown in FIG. 3 (SEQ ID NO: 24) are capable of blocking completely the entry of the sporozoites of *P. yoelii* into hepatic cells of rodents in vitro, unlike the antibodies directed against the circumsporozoite protein of *P. yoelii* and of *P. falciparum*.

The possibility of producing molecules according to the invention in large amounts as well as their properties of specific recognition of antibodies included among the most actively produced on infection of an individual by *P. falciparum* make the said molecules the reagents of choice for the in vitro diagnosis of malaria in an individual infected by *P. falciparum*.

The invention thus relates to a procedure for the in vitro detection of antibodies which correlate with malaria originating from the infection of an individual by *P. falciparum* in a tissue or biological fluid likely to contain them, this procedure comprising the placing of this tissue or biological fluid in contact with a molecule according to the invention under conditions which allow an in vitro immunological reaction between the said molecules and the antibodies possibly present in the tissue or biological fluid to occur, and the in vitro detection of the antigen-antibody complexes possibly formed.

The biological fluid is preferably constituted by a human serum.

Any standard procedure may be used to carry out such a detection.

As an example, a preferred method makes use of immunoenzymatic processes according to the ELISA procedure, or immunofluorescent or radioimmunological (RIA) or equivalent procedures.

Thus, the invention also relates to any molecule according to the invention labelled with the aid of a suitable label of the enzymatic, fluorescent, radioactive, etc . . . type.

Such methods comprise for example the following steps:
the loading of defined quantities of a polypeptide composition according to the invention into the wells of a microtitration plate,
introduction into the said wells of increasing dilutions of serum requiring diagnosis,
incubation of the microplate,
repeated rinsings of the microplate,
introduction into the wells of the microplate labelled antibodies against the immunoglobulins of the blood, the labelling of these antibodies having been carried out with the aid of an enzyme selected from those which are capable of hydrolysing a substrate and of thus changing the absorption of the latter, at least at one particular wavelength,
detection of the quantity of substrate hydrolysed, in comparison with a control.

The invention also relates to kits for the in vitro diagnosis of malaria caused by *P. falciparum* which contain:
a polypeptide composition according to the invention,
the reagents for the constitution of the medium suitable for carrying out the immunological reaction,
the reagents necessary for the detection of the antigen-antibody complexes produced by the immunological reaction, these reagents may also be labelled, or be capable of being recognized in turn by a labelled reagent, more particularly in the case in which the above-mentioned polypeptide composition is not labelled.
a reference tissue or biological fluid lacking antibodies recognized by the above-mentioned polypeptide composition.

The invention relates to the antibodies themselves formed again the polypeptides of the invention.

It will be obvious that these antibodies are not limited to polyclonal antibodies.

The invention also applies to any monoclonal antibody produced by any hybridoma capable of being formed by standard methods from the spleen cells of an animal, in particular a mouse or a rat, immunised against one of the purified peptides of the invention, on the one hand, and cells of a suitable myeloma cell line, on the other, and which can be selected for its capacity to produce monoclonal antibodies which recognize the polypeptide initially used for the immunization of the animals.

The invention also relates to a method for the in vitro diagnosis of malaria in an individual likely to be infected by *P. falciparum* which comprises the placing of a tissue or biological fluid taken from an individual in contact with antibodies such as those described above under conditions which allow an in vitro immunological reaction between the said antibodies and the proteins specific for *P. falciparum* possibly present in the biological tissue to occur, and the in vitro detection of the antigen antibody complexes possibly formed.

Consequently, the subject of the invention is a kit for the in vitro diagnosis of malaria containing
antibodies such as those described above,
the reagents for making up to appropriate medium for carrying out the immunological reaction,
the reagents making possible the detection of the antigen-antibody complexes produced by the immunological reaction, these reagents may also be labelled, or be capable of being recognized in turn by a labelled reagent, more particularly in the case in which the above-mentioned polypeptide composition is not labelled.

The invention also relates to a nucleotide detection probe characterized in that it is composed of all or part of one of the nucleotide sequences of the invention such as defined above.

More particularly the subject of the invention is an in vitro diagnostic method for malaria in an individual likely to be infected by *P. falciparum* which comprises the following steps:
possibly prior amplification of the quantity of nucleotide sequences according to the invention likely to be contained in the biological sample taken from the said individual, with the aid of two DNA primers selected in the manner indicated above, the placing of the above-mentioned biological sample in contact with a nucleotide probe such as that defined above under conditions which allow the production of a hybridization complex formed between the said probe and the said nucleotide sequence, the detection of the above-mentioned hybridization complex possibly formed.

As examples of nucleotide probes of the invention, mention should be made of the following sequences (SEQ ID NOS: 29 AND 30):

Most especially, the invention opens the door to the development of novel vaccinating principles against malaria originating from the infection of an individual by *P. falciparum*.

The invention also relates to the compositions prepared in the form of vaccines which contain either one or more peptides according to the invention or an oligomer of this or these peptide(s) or also a conjugate of this or these peptide(s) or oligomer with a carrier molecule, in combination with a suitable pharmaceutically acceptable vehicle and, optionally, with other active ingredients which vaccinate against malaria.

A particularly useful pharmaceutical composition of the invention is characterized in that it contains all or part of the peptide sequence defined by the amino acids situated at the positions 200 to 316 of FIG. 1, in combination with all or part of the peptide sequence shown in FIG. 3.

Advantageous pharmaceutical compositions are constituted by solutions, suspensions or injectable liposomes containing an efficacious dose of at least one product according to the invention. Preferably, these solutions, suspensions or liposomes are prepared in an isotonic sterilized aqueous phase, preferably a saline or glucose solution.

The invention relates more particularly to such suspensions, solutions or liposomes which can be administered by intradermal, intramuscular or subcutaneous injection or even by scarification.

It also relates to pharmaceutical compositions which can be administered by other routes, in particular the oral or rectal route, or also in the form of aerosols designed to come into contact with mucous membranes, in particular the ocular, nasal, pulmonary or vaginal mucous membranes.

Consequently, it relates to pharmaceutical compositions in which at least one of the products according to the invention is combined with pharmaceutically acceptable excipients, solid or liquid, suited to the composition of oral, ocular or nasal forms, or with excipients suited to the composition of the rectal forms of administration, or also with gelatinous excipients for vaginal administration. It also relates to isotonic liquid compositions containing at least one of the conjugates according to the invention, adapted to administration to mucous membranes, in particular ocular or nasal mucous membranes.

Advantageously, the vaccinating compositions according to the invention contain in addition a vehicle such as polyvinyl-pyrrolidone, which facilitates the administration of the vaccine. Instead of polyvinyl-pyrrolidone it is possible to use any other type of adjuvant in the classical sense which this expression used to connote, i.e., a substance which makes the absorption of the medicine easier or facilitates its action in the organism. As examples of other adjuvants of this latter type, mention should also be made of carboxymethylcellulose, the hydroxides and phosphates of aluminium, saponin or all other adjuvants of this type, well known to the specialist skilled in the art. Finally, if necessary, they contain an immunological adjuvant, in particular of the muramyl peptide type.

The invention also relates to pharmaceutical compositions containing as active substance at least one of the monoclonal or polyclonal antibodies previously defined in combination with a pharmaceutically acceptable vehicle.

The invention is obviously not limited to the embodiments described above as examples and the specialist skilled in the art may make modifications to them without exceeding the limits of the framework of the Claims given hereafter; in particular, some of the amino acids of the sequence of the peptides according to the invention may be replaced by isofunctional or isosteric amino acids; for example, one or more of the following substitutions may be envisaged:

Glu is replaced by Asp or Gln,

Leu is replaced by Ala, etc . . .

It is naturally understood that the peptides which result from such substitutions consist of equivalents of the peptides more particularly claimed provided that they themselves or oligomers or conjugates formed from these peptides exhibit similar immunogenic properties.

The invention also relates more particularly to the "chimeric proteins" which can be obtained by the procedures of genetic engineering, these chimeric proteins containing one or more of the peptide sequences of the invention, and being incorporated into or attached to a peptide fragment other than beta-galactosidase. This latter peptide fragment preferably has a molecular weight sufficient to reinforce the immunogenicity of the peptide sequences according to the invention and does not interfere immunologically with the expression of the desired immunogenicity.

Additional characteristics of the invention will also become apparent in the course of the description which follows of the conditions under which the polypeptides of the invention were obtained.

Sera derived from Europeans living in endemic areas and following a continuous prophylaxis with medicines directed against the schizonts of the blood stages (chloroquine) were selected and tested by using antigens of the sporozoite stage, the hepatic stage (LS antigen) and the blood stages. Most of these sera react with the antigens of all of the stages probably because the prophylaxis had been interrupted. Three sera taken from individuals who had resided in rural tropical Africa and who had ingested 100 ug of chloroquine per day without interruption for 23 to 26 years did not react with the antigens of the blood stages according to the immunofluorescence assay (IFA). However, these three sera possessed high titers of antibodies directed against the sporozoites and the LSA proteins (dilution IFA 1/3200 and 1/6400, respectively).

One of the three sera just mentioned, with reduced specificity, was used to screen a genomic DNA library constructed in the bacteriophage λgt 11 in the following manner:

1) Construction of the Genomic DNA Library of *Plasmodium falciparum*

The genomic DNA of clone 96 of the Thailand Tak9 strain of *P. falciparum* (Science, 212 137-138 (1981) was isolated by standard procedures.

Samples of 18 µg of DNA of *P. falciparum* were incubated at 15° C. in a 50 mM Tris HCl buffer, pH 7.5, 1 mM MnCl2, 20 pg/ml of bovine serum albumin with variable amounts of DNAase I (Boehringer Mannheim): 5 pg for 5 minutes or 3.5 pg for 5 or 10 minutes. After addition of 5 mM EDTA (ethylenediamine tetraacetic acid), the samples of DNA are pooled and purified by extraction with a phenol/chloroform/isoamyl alcohol mixture (25 V/24 V/1 V), then with ether. The DNA is concentrated by precipitation with ethanol at −20° C. in the presence of 2.5 M ammonium acetate.

45 µg of DNA thus treated was methylated by means of 180 U of EcoRI methylase (Biolabs) under the conditions recommended by the supplier, with the further addition of 5 mM DTT (dithiothreitol) for 15 minutes at 37° C. After purification of the DNA as above, 10 ug of DNA were incubated with 40 mM Tris HC1, pH 8.0, 10 mM ammonium sulfate, 10 mM 2-mercaptoethanol, 0.5 mM EDTA, 0.05 mM NAD (nicotinamide adenine dinucleotide) 0.1 mM dXTP (comprising the 4 deoxynucleosides triphosphates dATP, dCTP, dGTP and dTTP) in the presence of 10 U T4 DNA polymerase (PL Biochemicals) and 10 U of E. coli DNA ligase (Biolabs). The DNA was purified and concentrated as above.

8 µg of DNA were then ligated with 0.4 ug of an EcoR1 adapter or "linker" (EcoR1 phosphorylated adapter marketed by Biolabs) by means of 4 U T4 DNA ligase (Biotec) in a 50 mM Tris HCl buffer, pH 8.0, 10 mM $MgCl_2$, 20 mM DTT, 1 mM ATP, 50 µg/ml bovine serum albumin.

After incubation at 4° C. for 5 hours, 2 U T4 DNA ligase are added and the reaction is allowed to proceed at 4° C. for 16 hours. The tube is subjected to several cycles of freezing to −80° C./thawing to stop the reaction. The DNA is then diluted and the incubation buffer is adjusted so as to produce the conditions recommended by the supplier for the use of the enzyme EcoR1. 100 U of enzyme EcoR1(Promega Biotec) are added and incubated for 3 hours at 37° C. The reaction is stopped by heating for 10 minutes at 60° C., and the DNA is purified and concentrated as above.

The DNA is resuspended in 100 µl of 50 mM Tris HC buffer, pH 8.0, 1 mM EDTA and loaded on to a 5-20% sucrose gradient prepared in 25 mM sodium acetate, 10 mM EDTA and centrifuged in the Beckmann rotor SW 50.1 at 45,000 revolutions per minute for 150 minutes.

The fractions are analysed on agarose gel and those which contain the DNA fragments of a size included between about 300 bp and 2,500 bp are pooled, dialysed against 50 mM Tris HCl buffer, pH 8.0, 1 mM EDTA at 4° C. The DNA is concentrated by precipitation with ethanol. About 400 ng of this DNA were ligated to 1 µg of DNA of the vector). λgt11 (Proc. Natl. Acad. Sci., USA, 80, 1194-1198 (1983)) cut with EcoR1 and dephosphorylated (Protoclone from Promega Biotec) in a volume of 10 µl (in 50 mM Tris HC buffer, pH 8.0, 10 mM $MgC1_2$ 20 MM DTT, 1 mM ATP, 50 µg/ml bovine serum albumin) by 1 U T4 DNA ligase (Biotec).

The ligation products were encapsidated in vitro in E. coli extracts prepared from the bacterial strains constructed by B. Hohn (Methods Enzymol. 68, 299) according to the procedure described by Maniatis et al. (Molecular cloning, a laboratory manual, p. 264, Cold Spring Harbor Laboratory (1982)).

About 7 millions of recombinant bacteriophages were obtained.

2) Immunological Screening of the Bank

The recombinant bacteriophages were spread on a culture medium containing the indicator bacteria Y 1090 at a density of 50,000 plaques per 90 mm Petri dish, and incubated at 42° C. for 3 hours. A nitrocellulose filter (Schleicher & Schuell, BA 85) saturated with 0.01 M IPTG isopropyl-beta thiogalactopyranoside (Sigma) is deposited on the dishes which are incubated at 37° C. for 3 hours. When the incubations are complete, the nitrocellulose filters are removed and the Petri dishes are stored at 4° C.

The nitrocellulose filters are placed in a bath of TL buffer: 50 mM Tris HC pH 8.0, 150 mM NaC 5% skimmed milk, 0.05% Tween 20 (Sigma). The filters are incubated for 15 hours at 4° C. in TL buffer, then twice for 15 minutes at 20° C. They are then incubated for one hour with a pool of human immune antisera directed against the antigens of all stages of development of P. falciparum treated beforehand to deplete it of anti E. coli antibodies according to the procedure described by Ozaki et al. (J. Immunol. Methods, 89, 213-219, 1986). The pool of .human antisera was used at a dilution of 1/200 in TL buffer. The incubation was carried out at 20° C. for 1 hour. The filters were washed 4 times with the TL buffer, then incubated with anti-human immunoglobulin antibodies conjugated to horseradish peroxidase (Biosys) and iodinated with $^{125}I$ for 1 hour at 20° C. After several washings with TL buffer, followed by 50 mM Tris HCl buffer, pH 8.0, 150 mM NaCl, the enzymatic activity of the peroxidase is revealed (Ozaki et al., previously cited), the filters are dried in air and autoradiographied using Kodak film Royal X-OMat AR with an amplifying screen.

A collection of about 1200 clones of recombinant bacteriophages was established by selecting the lysis plaques corresponding to the positive signals. These clones were then subjected to a second cycle of immunological screening by using this time one of the three human sera previously described and exhibiting few or no antibodies directed against the erythrocytic forms of P. falciparum and a high titer against the sporozoite and hepatic forms of the parasite. This immunological screening was carried out according to the protocol described above. This serum has led to the identification of about recombinant 120 clones out of 1200 tested.

The human antibodies which react with the antigenic determinants expressed by the recombinant clones were purified by means of their affinity for the recombinant proteins according to the procedure described by Ozaki et al. (previously cited). These specific antibodies were incubated with preparations of parasites at different stages of development (sporozoite, hepatic stage or erythrocytic stages), and the reaction was studied by means of indirect immunofluorescence.

The recombinant clones on which the antibodies specific for the hepatic stage are retained by affinity and which thus express determinants intrinsic to this stage were studied: they are the clones DO 307, DG 199 and Dg 145. These specific antibodies of these three clones react specifically with the hepatic schizonts such as can be obtained alter infection of human or monkey hepatocytes by sporozoites of P. falciparum the localization of the fluorescence was determined to be identical with that considered to be characteristic of LSA.

The species- and stage-specificity of the 3 clones DG 145, DG 199 and DG 307 were tested in the following manner. Firstly, it was determined that the same antibodies purified by affinity and which react by IFA (or also which are IFA-positive) with LSA do not react with dried or moist preparations of sporozoites, nor with the antigens of the blood stages, whether they are tested by IFA with parasites fixed in acetone or by immunoblotting by using proteins of all of the stages extracted with SDS. The antibodies purified by affinity do not react with the antigens of the hepatic stage of P. yoelii nor with the hepatic schizonts of P. vivax prepared from Saimiri sciureus monkeys.

Secondly, the recombinant proteins of DG 145, DG 199 and DG 307 do not react with the sera obtained from two patients suffering from malaria (caused by P. falciparum by accidental transfusion and which, by definition, thus do not have antibodies against the antigens specific for the earlier stages (sporozoites and antigens of the hepatic stage). These proteins do not react with two monoclonal antibodies which recognize the CS tetrapeptide, with the sera of mice immunised with the recombinant CS antigens R32t and 32 (Science, 228 958 (1985)). Furthermore, the recombinant proteins did not react with human antisera directed against P.

vivax (although the sera were positive with the hepatic schizonts of *P. vivax*, *P. ovale* and *P. cynomolgi* (Ann. Soc. Belg. Med. Trop., 60, 348 (1980)) when they are tested by the technique of immunodot blots, whereas they are positive with all of the human anti-*P. falciparum* sera tested.

Within this sub-population of 120 clones mentioned above, an immunological screening procedure using antibodies purified by affinity to the clone DG307 (or 145, or 199) leads to the detection of about 40 clones out of 120 apparently exhibiting the characteristic epitope of the LSA and defined by the basic structure of 17 amino acids cited above.

Similarly, identification procedures based on hybridization with the aid of DNA fragments from the same clones (DG307) make it possible to identify these repetitive structures in the same clones as those identified by the immunological assays.

A complementary screening of the sub-population of 40 clones belonging to this family of the LSA antigen was used to identify other parts of the gene containing sequences distinct from those defined by the repeats of 7 amino acids. For this complementary screening sera identified as not reacting with the repeats of the 17 amino acids but positive in indirect immunofluorescence with the peripheral structure of the hepatic schizont in which the LSA antigen is situated, were employed. Within the family of the 40 clones of the LSA, these sera were found to be positive for several of them, and one of the clones containing the largest insert, designated DG536, was selected and studied in detail.

Other clones, DG538, DG750 and DG443 were studied. The clones DG750 and DG443 contain the major part of the non repetitive 5' sequence of the LSA gene.

The insert of 951 base pairs was purified and recloned in the bacteriophage M13 mp19. The DNA sequence and the genomic organization of the LSA gene were then determined. FIG. 1 (SEQ ID NO: 31) shows that the clone contains a sequence of 209 amino acids at the 5' end corresponding to a series of 12 repeats of 17 amino acids, similar to that described in the article by Guérin-Marchand et al. (Nature, mentioned above) and then contains a set of 106 amino acids, the structure of which is not repetitive.

As can be seen in FIG. 1 (SEQ ID NO: 31), the motif of 17 amino acids is in two repeats (cf. motif corresponding to the positions 35 to 51, and that corresponding to the positions 137 to 153 of FIG. 1) identical with that described in the article by Guérin-Marchand et al. and the other repeats exhibit a substitution of a leucine by an arginine (cf. positions 8, 59, 76, 110, 127, 161, 178 and 195 of FIG. 1) (SEQ ID NO: 31), a substitution of a glutamic acid by an aspartic acid (cf. positions 23 and 91 of FIG. 1 (SEQ ID NO: 31)) as well as a substitution of a serine by an arginine (cf. position 205 of FIG. 1 (SEQ ID NO: 31)).

It was possible to measure the size of the native protein of the LSA in the parasite after surmounting great difficulties. Hepatic schizonts of *P. falciparum* were produced in vitro by infection of human hepatocytes from a primary culture with salivary glands of mosquitoes containing sporozoites according to the procedure described in Mazier et al. (Science No. 227, p440, 1985). Alter 7 days of culture, the infected cells are recovered and used to prepare an extract analysed on polyacrylamide gel containing SDS and transferred to nitrocellulose. The hepatic antigens are then revealed by an antibody purified by affinity to the repeats of the 17 amino acids of the LSA already mentioned. These antibodies label a protein of molecular weight of 200,000 Daltons.

The hybridization of the clone DG307 with the DNA fragments of *P. falciparum* obtained by digestion with a restriction enzyme, the Mung bean nuclease, which under the conditions described by McCutchans (NAR, 16, 14, 6883-6896, 1988) is capable of cutting each end of the genes of the parasite, reveals a unique band of molecular weight of 5 K bases consistent with the size of the native protein measured in the parasite extract.

In electron microscopy of the hepatic schizonts obtained by injection of sporozoites of chimpanzees, the labelling of the anti-LSA antibodies purified by affinity, visualized by a second antibody labelled with colloidal gold, reveals that the LSA molecule is distributed: a) at the stage of the hepatic trophozoite and the young schizont, in vacuoles containing granules which open and discharge their contents into the parasitophorous vacuole, b) at the stage of the 5 days old immature schizont, at the periphery of the hepatic schizont in the granules present in the parasitophorous vacuole of the parasite, c) in the 6 to 7 days old mature schizonts, in the parasitophorcus vacuole as well as between the pseudo cytomers of the schizont, then finally surrounding the merozoites in process of formation.

The study of the immunological response of subjects exposed to malaria as well as animals immunized with the recombinant and/or synthetic proteins makes it possible to specify the biological function of the LSA protein and of certain segments of this protein, in particular those contained in the synthetic peptides.

The immunization of mice with the LSA-R-NR proteins and the study of the response of the lymphocytes of these mice, as well the immunization with the LSA-R peptides of mice of different haplotypes with peptides LSA-R, LSA-J and LSA-NR, and finally the study of the responses of the lymphocytes of the subjects exposed to malaria towards the LSA-R peptides had shown that a T epitope for man and the mouse is not defined by the repetitive part of the LSA molecule. More detailed studies show the existence of a T epitope in the LSA-R peptide. As had been shown previously, the LSA-R peptide constitutes an excellent B epitope for man and the mouse, defined by the repetitive part of the LSA molecule, and the complementary results obtained since in more than 500 individuals exposed to malaria show that this epitope is recognized by the antibodies of about 95% of the subjects studied, in Senegal, Upper Volta, Madagascar and Kenya.

The preliminary study of the lymphocytes of 5 adult African subjects exposed to malaria, subsequently confirmed by the detailed study of the response of the peripheral lymphocytes of more than 200 adult African subjects exposed to malaria as well as the lymphocytes of chimpanzees (Pan troglodytes) immunised by the recombinant protein LSA-R-NR (clone D0536), revealed that a T epitope of the LSA molecule is defined by the amino acid sequence contained in the synthetic peptide LSA-NR. Two other T epitopes are contained in the sequences of the synthetic peptides LSA-J and LSA-R (in total 39% of positive responses to the T epitopes of the LSA in Madagascar and 83% in Senegal). Proliferative responses of the human lymphocytes and the lymphocytes of an immunised chimpanzee were observed after stimulation by these three peptides, a) in the chimpanzee 60% of the lymphocytic lines obtained are of the $CD8^+$ phenotype, b) in the mouse, the injection of one or other of these peptides makes it possible immunologically to "prime" the immune system of the mouse and to obtain the production of a high level of antibodies against the B epitope of the LSA-R peptide after the injection of the recombinant protein LSA R-NR. The identification of those epitopes capable of stimulating the T lymphocytes is of great important in as much as it has been established in the malaria of rodents that the protection induced by irradiated sporozoites is dependent on the production of lymphocytes cytotoxic for the infected hepatocyte, and capable of destroying them.

Furthermore, the study of 20 sera of African subjects also shows that the peptide LSA-NR defines a B epitope, distinct front that which is found in the repeats, recognized by about 65% of the subjects studied.

On the other hand, the peptide LSA-TER does not constitute a significant B epitope, it is rarely recognized by the antibodies of the subjects studied.

The potential usefulness of the T epitopes of the LSA, in particular those contained in the non-repetitive part, is, in addition strongly reinforced by the results obtained in the chimpanzee:

in the chimpanzee which bas been immunised by three injections at intervals of 15 days of a mixture of two recombinant proteins adsorbed on alum, the recombinant protein LSA-R-RN (clone DG536) on the one hand and the recombinant protein designated DGi729S (clone DG729S which forms part of the 120 clones mentioned above) on the other, it was possible to obtain several significant results:
  the production of antibodies specific for each of the two recombinant molecules, i.e. which react with the protein LSA-R-NR and the synthetic peptides, as well as with the recombinant protein 729S, was detected.
  a specific proliferative response of the lymphocytes was obtained towards the peptide LSA-NR and also to the peptides LSA-J and LSA-TER. Sixty percent of the proliferating lymphocytes are of the $CD8^+$ phenotype, which corresponds in particular to cytotoxic T lymphocytes.
  After immunization of the chimpanzees, a test infection by intravenous injection of 28 millions of sporozoites of *P. falciparum* was carried out on an immunized chimpanzee and in a control chimpanzee (which received an unrelated control recombinant protein) and liver biopsies were made on day 6 after injection. The examination of the biopsies showed the existence of a cellular reaction, lympho-monocytic, around the hepatic schizonts, infiltrating the schizonts and capable of destroying them. Such images were net observed in the chimpanzee which had received the control antigen.

This cellular reaction reveals the existence of T epitopes in the injected molecules 729S and LSA-R-NR (DG536) which are capable of being expressed in the injected molecules, capable of being expressed by The hepatic schizonts and of inducing a cellular afflux; this result is in agreement with the results of the lymphocytic proliferation assays; finally it shows that the immune response induced by the injected recombinant proteins is capable, upon penetration of the parasite, of inducing a cellular afflux, itself capable of contributing to the defence of the organism by destroying the parasites located within the hepatocytes.

A specific proliferative response of the lymphocytes was also obtained towards the peptides 729S-NRI and 729S-NRII.

The cytolytic capacity of the lymphocytes of this immunized and protected chimpanzee was measured in vitro in the following manner: lymphocyte lines were produced by in vitro stimulation with the peptides LSA-NR and LSA-J as well as with 729-NRI and NRII in the presence of interleukin 2. These lines were maintained for 4 weeks by restimulation in the presence of autologous mononucleated cells from the same chimpanzee by the same peptides and interleukin 2. A cytolysis test was carried out by incubating the irradiated peripheral mononucleated cells of the chimpanzee with the same peptides, then after labelling with chromium 51, by incubating these cells with the lines produced. Release of the chromium 51 reflecting the destruction of the target cells was observed. These results demonstrate that the T epitopes, defined above, are capable of activating the cytolytic T lymphocytes specific for the polypeptide sequences in question.

The antigenic and/or immunological specificities of the polypeptides of the invention are the following:
  the polypeptide 536:
    is recognized:
      by originating from subjects with malaria,
      by sera of chimpanzees immunized with the recombinant-complete protein 536,
      co-reacts with the polypeptides described in Guerin-Marchand et al. (Nature, cited above) by the intermediary of the repeat sequences,
      induces the function of antibodies (presence of B epitopes)
      induces proliferative responses of lymphocytes (presence of T epitope) in the chimpanzee and in man.
  the polypeptides NR and TER include a major T epitope and a B epitope for man as for the immunized animal (mouse and chimpanzee),
  the polypeptide LSA-J includes a B epitope distinct from that of the 17 amino acid repeat probably on account of the substitution of S by R, and contains a T epitope recognized in man and the chimpanzee.
The recombinant protein 7295:
is recognized
  by antibodies of subjects exposed to malaria,
  by sera of chimpanzees and mice immunized by the protein 729S
is better recognized by the individuals capable of resisting infection by malaria than by those who do not resist (in the north of Senegal, the inventors have administered a radical course of treatment of chloroquine to 100 individuals, and followed the repositivation of the blood during the period of transmission, from September to December a) in the subjects who are not positive, no antibody against the protein 7295 was detected, b) in more than half of those who had not become positive again, there existed a high titer response to the protein 729S).
is recognized by the sera of three individuals who had been vaccinated by multiple injections of sporozoites of *P. falciparum* and who had resisted a test injection of non-irradiated virulent sporozoites, but is not recognized by the sera of four other individuals who had been vaccinated by multiple injections of sporozoites irradiated with high doses of radiation and who had not resisted the same test injections of non-irradiated sporozoites. This recognition relates in particular to the reaction of the antibodies with the polypeptide 729S-NRII. Hence there exists a tight correlation between the immune response directed against the molecule 729S and the protection induced against malaria in maxn.

The polypeptides 729S-NRI and 729S-NRII bear additionally major T epitopes which are recognized by the majority of these subjects whose lymphocytes were studied recently in Madagascar and Senegal (18 out of 20 positives studied in Madagascar and 26 out of 46 studied in Senegal).

The polypeptide 729S-R also contains a T epitope recognized by high proportion of individuals of Senegalese and Madagascan origin (30 to 60% of the individuals studied) but in addition it defines a major B epitope of the molecule because the antibodies of 96 to 100% of the subjects studied in Senegal, Cameroon and Madagascar recognize this peptide and because the antibody titer observed is extremely high.

It will immediately be apparent to the specialist skilled in the art that in the nucleotide sequences mentioned above, some of the nucleotides may be replaced by others on account of the degeneracy of the genetic code without the peptides being modified in any way. All of these nucleotide sequences as well as those which code for polypeptides which differ from former by one or more amino acids without their intrinsic inmunogenic activity being similarly modified, form part of the invention. Naturally, the same holds for the nucleotide sequences which may be reconstituted and which are capable of coding for oligomers such as defined hereafter. The monomeric motifs are linked directly end to end or through the intermediary of peptide sequences without any effect on the immunogenic properties of the oligomers thus formed.

Bacteria harbouring the above-mentioned clones DG199 and DG307 were deposited with the Collection Nationale des Cultures de Microorganismes at the Pasteur Institute in Paris (CNCM) on 22 Jul. 1986 under the numbers I-580 and I-581, respectively. Bacteria harbouring the clone DG145 was deposited on 15 September 1986 under the number I 606. he clones DG 536 and DG 729 were deposited on 17 Jan. 1991 under the number I-1027 and on 17 Jan. 1991 under the number I-1028, respectively.

In the preceding formula, use is made of the international nomenclature which designates each of the naturally occurring amino acids by a single letter, in particular according to the table of correspondences which follows:

M Methionine
L Leucine
I Isoleucine
V Valine
F Phenylalanine
S Serine
P Proline
T Threonine
A Alanine
Y Tyrosine
H Histidine
Q Glutaniine
N Asparagine
K Lysine
D Aspartic acid
E Glutamic acid
C Cysteine
W Tryptophan
R Arginione
G Glycine

The invention claimed is:

1. A purified polypeptide comprising at least one T epitope from a liver-stage specific protein produced by *P. falciparum*, wherein said at least one epitope consists of the amino acid sequence of SEQ ID NO: 19 and is preceded by one or more of the amino acid sequences of SEQ ID NOS: 2 to 18, and wherein X1 is Ser or Arg; X2 is Glu or Asp; X3 is Arg or Leu; and X4 is Glu or Gly.

2. A method for in vitro diagnosis of malaria in an individual comprising: placing a tissue or a biological fluid taken from said individual in contact with the polypeptide of claim 1, under conditions allowing an in vitro immunological reaction to occur between the polypeptide and antibodies that may be present in the tissue or biological fluid, and detecting in vitro the antigen-antibody complexes formed.

* * * * *

```
                      SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 8
         (D) OTHER INFORMATION: /note= "Amino Acid 8 wherein Xaa is
             Glu or Gly."

(x) PUBLICATION INFORMATION:
         (H) DOCUMENT NUMBER: WO 92/13884
         (J) PUBLICATION DATE: 20-AUG-1992

(xi) SEQUENCE DESCRIPTION: SEQ ID NO:1:

Leu Ala Lys Glu Lys Leu Gln Xaa Gln Gln Ser Asp Leu Glu Gln Glu
1               5                  10                  15

Arg (2) INFORMATION FOR SEQ ID NO:2:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
```

```
            (B) LOCATION: 1
            (D) OTHER INFORMATION: /note= "Amino Acid 1 wherein Xaa is
                Ser or Arg."

(ix) FEATURE:
            (A) NAME/KEY: Peptide
            (B) LOCATION: 6
            (D) OTHER INFORMATION: /note= "Amino Acid 6 wherein Xaa is
                Glu or Asp."

(ix) FEATURE:
            (A) NAME/KEY: Peptide
            (B) LOCATION: 8
            (D) OTHER INFORMATION: /note= "Amino Acid 8 wherein Xaa is
                Arg or Leu."

(ix) FEATURE:
            (A) NAME/KEY: Peptide
            (B) LOCATION: 15
            (D) OTHER INFORMATION: /note= "Amino Acid 15 wherein Xaa
                is Glu or Gly."

(x) PUBLICATION INFORMATION:
            (H) DOCUMENT NUMBER: WO 92/13884
            (J) PUBLICATION DATE: 20-AUG-1992

(xi) SEQUENCE DESCRIPTION: SEQ ID NO:2:

Xaa Asp Leu Glu Gln Xaa Arg Xaa Ala Lys Glu Lys Leu Gln Xaa Gln
1               5                  10                  15

Gln (2) INFORMATION FOR SEQ ID NO:3:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 2
            (D) OTHER INFORMATION: /note= "Amino Acid 2 wherein Xaa is
                Ser or Arg."

(ix) FEATURE:
            (A) NAME/KEY: Peptide
            (B) LOCATION: 7
            (D) OTHER INFORMATION: /note= "Amino Acid 7 wherein Xaa is
                Glu or Asp."

(ix) FEATURE:
            (A) NAME/KEY: Peptide
            (B) LOCATION: 9
            (D) OTHER INFORMATION: /note= "Amino Acid 9 wherein Xaa is
                Arg or Leu."

(ix) FEATURE:
            (A) NAME/KEY: Peptide
            (B) LOCATION: 16
            (D) OTHER INFORMATION: /note= "Amino Acid 16 wherein Xaa
                is Glu or Gly."

(x) PUBLICATION INFORMATION:
            (H) DOCUMENT NUMBER: WO 92/13884
            (J) PUBLICATION DATE: 20-AUG-1992

(xi) SEQUENCE DESCRIPTION: SEQ ID NO:3:

Gln Xaa Asp Leu Glu Gln Xaa Arg Xaa Ala Lys Glu Lys Leu Gln Xaa
1               5                  10                  15

Gln
```

```
(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 3
        (D) OTHER INFORMATION: /note= "Amino Acid 3 wherein Xaa is
            Ser or Arg."

(ix) FEATURE:
        (A) NAME/KEY: Peptide
        (B) LOCATION: 8
        (D) OTHER INFORMATION: /note= "Amino Acid 8 wherein Xaa is
            Glu or Asp."

(ix) FEATURE:
        (A) NAME/KEY: Peptide
        (B) LOCATION: 10
        (D) OTHER INFORMATION: /note= "Amino Acid 10 wherein Xaa
            is Arg or Leu."

(ix) FEATURE:
        (A) NAME/KEY: Peptide
        (B) LOCATION: 17
        (D) OTHER INFORMATION: /note= "Amino Acid 17 wherein Xaa
            is Glu or Gly."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:4:

Gln Gln Xaa Asp Leu Glu Gln Xaa Arg Xaa Ala Lys Glu Lys Leu Gln
1               5                   10                  15

Xaa (2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Amino Acid 1 wherein Xaa is
            Glu or Gly."

(ix) FEATURE:
        (A) NAME/KEY: Peptide
        (B) LOCATION: 4
        (D) OTHER INFORMATION: /note= "Amino Acid 4 wherein Xaa is
            Ser or Arg."

(ix) FEATURE:
        (A) NAME/KEY: Peptide
        (B) LOCATION: 9
        (D) OTHER INFORMATION: /note= "Amino Acid 9 wherein Xaa is
            Glu or Asp."

(ix) FEATURE:
        (A) NAME/KEY: Peptide
        (B) LOCATION: 11
        (D) OTHER INFORMATION: /note= "Amino Acid 11 wherein Xaa
```

-continued

```
            is Arg or Leu."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:5:

Xaa Gln Gln Xaa Asp Leu Glu Gln Xaa Arg Xaa Ala Lys Glu Lys Leu
1               5                   10                  15

Gln (2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 2
        (D) OTHER INFORMATION: /note= "Amino Acid 2 wherein Xaa is
            Glu or Gly."

(ix) FEATURE:
        (A) NAME/KEY: Peptide
        (B) LOCATION: 5
        (D) OTHER INFORMATION: /note= "Amino Acid 5 wherein Xaa is
            Ser or Arg."

(ix) FEATURE:
        (A) NAME/KEY: Peptide
        (B) LOCATION: 10
        (D) OTHER INFORMATION: /note= "Amino Acid 10 wherein Xaa
            is Glu or Asp."

(ix) FEATURE:
        (A) NAME/KEY: Peptide
        (B) LOCATION: 12
        (D) OTHER INFORMATION: /note= "Amino Acid 12 wherein Xaa
            is Arg or Leu."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:6:

Gln Xaa Gln Gln Xaa Asp Leu Glu Gln Xaa Arg Xaa Ala Lys Glu Lys
1               5                   10                  15

Leu (2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 3
        (D) OTHER INFORMATION: /note= "Amino Acid 3 wherein Xaa is
            Glu or Gly."

(ix) FEATURE:
        (A) NAME/KEY: Peptide
        (B) LOCATION: 6
```

(D) OTHER INFORMATION: /note= "Amino Acid 6 wherein Xaa is
                        Ser or Arg."

(ix) FEATURE:
                    (A) NAME/KEY: Peptide
                    (B) LOCATION: 11
                    (D) OTHER INFORMATION: /note= "Amino Acid 11 wherein Xaa
                        is Glu or Asp."

(ix) FEATURE:
                    (A) NAME/KEY: Peptide
                    (B) LOCATION: 13
                    (D) OTHER INFORMATION: /note= "Amino Acid 13 wherein Xaa
                        is Arg or Leu."

(x) PUBLICATION INFORMATION:
                    (H) DOCUMENT NUMBER: WO 92/13884
                    (J) PUBLICATION DATE: 20-AUG-1992

(xi) SEQUENCE DESCRIPTION: SEQ ID NO:7:

Leu Gln Xaa Gln Gln Xaa Asp Leu Glu Gln Xaa Arg Xaa Ala Lys Glu
1               5                  10                  15

Lys (2) INFORMATION FOR SEQ ID NO:8:

(i) SEQUENCE CHARACTERISTICS:
                    (A) LENGTH: 17 amino acids
                    (B) TYPE: amino acid
                    (C) STRANDEDNESS: single
                    (D) TOPOLOGY: linear (ii) MOLECULE TYPE: peptide (ix) FEATURE:
                    (A) NAME/KEY: Peptide
                    (B) LOCATION: 4
                    (D) OTHER INFORMATION: /note= "Amino Acid 4 wherein Xaa is
                        Glu or Gly."

(ix) FEATURE:
                    (A) NAME/KEY: Peptide
                    (B) LOCATION: 7
                    (D) OTHER INFORMATION: /note= "Amino Acid 7 wherein Xaa is
                        Ser or Arg."

(ix) FEATURE:
                    (A) NAME/KEY: Peptide
                    (B) LOCATION: 12
                    (D) OTHER INFORMATION: /note= "Amino Acid 12 wherein Xaa
                        is Glu or Asp."

(ix) FEATURE:
                    (A) NAME/KEY: Peptide
                    (B) LOCATION: 14
                    (D) OTHER INFORMATION: /note= "Amino Acid 14 wherein Xaa
                        is Arg or Leu."

(x) PUBLICATION INFORMATION:
                    (H) DOCUMENT NUMBER: WO 92/13884
                    (J) PUBLICATION DATE: 20-AUG-1992

(xi) SEQUENCE DESCRIPTION: SEQ ID NO:8:

Lys Leu Gln Xaa Gln Gln Xaa Asp Leu Glu Gln Xaa Arg Xaa Ala Lys
1               5                  10                  15

Glu (2) INFORMATION FOR SEQ ID NO:9:

(i) SEQUENCE CHARACTERISTICS:
                    (A) LENGTH: 17 amino acids
                    (B) TYPE: amino acid
                    (C) STRANDEDNESS: single

```
        (D) TOPOLOGY: linear (ii) MOLECULE TYPE: peptide (ix) FEATURE:
        (A) NAME/KEY: Peptide
        (B) LOCATION: 5
        (D) OTHER INFORMATION: /note= "Amino Acid 5 wherein Xaa is
            Glu or Gly."

(ix) FEATURE:
        (A) NAME/KEY: Peptide
        (B) LOCATION: 8
        (D) OTHER INFORMATION: /note= "Amino Acid 8 wherein Xaa is
            Ser or Arg."

(ix) FEATURE:
        (A) NAME/KEY: Peptide
        (B) LOCATION: 13
        (D) OTHER INFORMATION: /note= "Amino Acid 13 wherein Xaa
            is Glu or Asp."

(ix) FEATURE:
        (A) NAME/KEY: Peptide
        (B) LOCATION: 15
        (D) OTHER INFORMATION: /note= "Amino Acid 15 wherein Xaa
            is Arg or Leu."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:9:

Glu Lys Leu Gln Xaa Gln Gln Xaa Asp Leu Glu Gln Xaa Arg Xaa Ala
1               5                  10                  15

Lys (2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 6
        (D) OTHER INFORMATION: /note= "Amino Acid 6 wherein Xaa is
             Glu or Gly."

(ix) FEATURE:
        (A) NAME/KEY: Peptide
        (B) LOCATION: 9
        (D) OTHER INFORMATION: /note= "Amino Acid 9 wherein Xaa is
            Ser or Arg."

(ix) FEATURE:
        (A) NAME/KEY: Peptide
        (B) LOCATION: 14
        (D) OTHER INFORMATION: /note= "Amino Acid 14 wherein Xaa
            is Glu or Asp."

(ix) FEATURE:
        (A) NAME/KEY: Peptide
        (B) LOCATION: 16
        (D) OTHER INFORMATION: /note= "Amino Acid 16 wherein Xaa
            is Arg or Leu."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:10:
```

```
Lys Glu Lys Leu Gln Xaa Gln Gln Xaa Asp Leu Glu Gln Xaa Arg Xaa
1               5                   10                  15

Ala
```

(2) INFORMATION FOR SEQ ID NO:11:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 7
        (D) OTHER INFORMATION: /note= "Amino Acid 7 wherein Xaa is
            Glu or Gly."

(ix) FEATURE:
        (A) NAME/KEY: Peptide
        (B) LOCATION: 10
        (D) OTHER INFORMATION: /note= "Amino Acid 10 wherein Xaa
            is Ser or Arg."

(ix) FEATURE:
        (A) NAME/KEY: Peptide
        (B) LOCATION: 15
        (D) OTHER INFORMATION: /note= "Amino Acid 15 wherein Xaa
            is Glu or Asp."

(ix) FEATURE:
        (A) NAME/KEY: Peptide
        (B) LOCATION: 17
        (D) OTHER INFORMATION: /note= "Amino Acid 17 wherein Xaa
            is Arg or Leu."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:11:

```
Ala Lys Glu Lys Leu Gln Xaa Gln Gln Xaa Asp Leu Glu Gln Xaa Arg
1               5                   10                  15

Xaa
```

(2) INFORMATION FOR SEQ ID NO:12:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Amino Acid 1 wherein Xaa is
            Arg or Leu."

(ix) FEATURE:
        (A) NAME/KEY: Peptide
        (B) LOCATION: 8
        (D) OTHER INFORMATION: /note= "Amino Acid 8 wherein Xaa is
            Glu or Gly."

(ix) FEATURE:
        (A) NAME/KEY: Peptide
        (B) LOCATION: 11
        (D) OTHER INFORMATION: /note= "Amino Acid 11 wherein Xaa is Ser or Arg."

(ix) FEATURE:
         (A) NAME/KEY: Peptide
         (B) LOCATION: 16
         (D) OTHER INFORMATION: /note= "Amino Acid 16 wherein Xaa
             is Glu or Asp."

(x) PUBLICATION INFORMATION:
         (H) DOCUMENT NUMBER: WO 92/13884
         (J) PUBLICATION DATE: 20-AUG-1992

(xi) SEQUENCE DESCRIPTION: SEQ ID NO:12:

Xaa Ala Lys Glu Lys Leu Gln Xaa Gln Gln Xaa Asp Leu Glu Gln Xaa
1               5                  10                  15

Arg (2) INFORMATION FOR SEQ ID NO:13:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 2
         (D) OTHER INFORMATION: /note= "Amino Acid 2 wherein Xaa is
             Arg or Leu."

(ix) FEATURE:
         (A) NAME/KEY: Peptide
         (B) LOCATION: 9
         (D) OTHER INFORMATION: /note= "Amino Acid 9 wherein Xaa is
             Glu or Gly."

(ix) FEATURE:
         (A) NAME/KEY: Peptide
         (B) LOCATION: 12
         (D) OTHER INFORMATION: /note= "Amino Acid 12 wherein Xaa
             is Ser or Arg."

(ix) FEATURE:
         (A) NAME/KEY: Peptide
         (B) LOCATION: 17
         (D) OTHER INFORMATION: /note= "Amino Acid 17 wherein Xaa
             is Glu or Asp."

(x) PUBLICATION INFORMATION:
         (H) DOCUMENT NUMBER: WO 92/13884
         (J) PUBLICATION DATE: 20-AUG-1992

(xi) SEQUENCE DESCRIPTION: SEQ ID NO:13:

Arg Xaa Ala Lys Glu Lys Leu Gln Xaa Gln Gln Xaa Asp Leu Glu Gln
1               5                  10                  15

Xaa (2) INFORMATION FOR SEQ ID NO:14:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1

(D) OTHER INFORMATION: /note= "Amino Acid 1 wherein Xaa is
    Glu or Asp."

(ix) FEATURE:
    (A) NAME/KEY: Peptide
    (B) LOCATION: 3
    (D) OTHER INFORMATION: /note= "Amino Acid 3 wherein Xaa is
        Arg or Leu."

(ix) FEATURE:
    (A) NAME/KEY: Peptide
    (B) LOCATION: 10
    (D) OTHER INFORMATION: /note= "Amino Acid 10 wherein Xaa
        is Glu or Gly."

(ix) FEATURE:
    (A) NAME/KEY: Peptide
    (B) LOCATION: 13
    (D) OTHER INFORMATION: /note= "Amino Acid 13 wherein Xaa
        is Ser or Arg."

(x) PUBLICATION INFORMATION:
    (H) DOCUMENT NUMBER: WO 92/13884
    (J) PUBLICATION DATE: 20-AUG-1992

(xi) SEQUENCE DESCRIPTION: SEQ ID NO:14:

Xaa Arg Xaa Ala Lys Glu Lys Leu Gln Xaa Gln Gln Xaa Asp Leu Glu
1               5                   10                  15

Gln (2) INFORMATION FOR SEQ ID NO:15:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 2
        (D) OTHER INFORMATION: /note= "Amino Acid 2 wherein Xaa is
            Glu or Asp."

(ix) FEATURE:
        (A) NAME/KEY: Peptide
        (B) LOCATION: 4
        (D) OTHER INFORMATION: /note= "Amino Acid 4 wherein Xaa is
            Arg or Leu."

(ix) FEATURE:
        (A) NAME/KEY: Peptide
        (B) LOCATION: 11
        (D) OTHER INFORMATION: /note= "Amino Acid 11 wherein Xaa
            is Glu or Gly."

(ix) FEATURE:
        (A) NAME/KEY: Peptide
        (B) LOCATION: 14
        (D) OTHER INFORMATION: /note= "Amino Acid 14 wherein Xaa
            is Ser or Arg."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:15:

Gln Xaa Arg Xaa Ala Lys Glu Lys Leu Gln Xaa Gln Gln Xaa Asp Leu
1               5                   10                  15

Glu (2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 3
        (D) OTHER INFORMATION: /note= "Amino Acid 3 wherein Xaa is
            Glu or Asp."

(ix) FEATURE:
        (A) NAME/KEY: Peptide
        (B) LOCATION: 5
        (D) OTHER INFORMATION: /note= "Amino Acid 5 wherein Xaa is
            Arg or Leu."

(ix) FEATURE:
        (A) NAME/KEY: Peptide
        (B) LOCATION: 12
        (D) OTHER INFORMATION: /note= "Amino Acid 12 wherein Xaa
            is Glu or Gly."

(ix) FEATURE:
        (A) NAME/KEY: Peptide
        (B) LOCATION: 15
        (D) OTHER INFORMATION: /note= "Amino Acid 15 wherein Xaa
            is Ser or Arg."

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:16:

```
Glu Gln Xaa Arg Xaa Ala Lys Glu Lys Leu Gln Xaa Gln Gln Xaa Asp
1               5                   10                  15

Leu
```

(2) INFORMATION FOR SEQ ID NO:17:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 4
        (D) OTHER INFORMATION: /note= "Amino Acid 4 wherein Xaa is
            Glu or Asp."

(ix) FEATURE:
        (A) NAME/KEY: Peptide
        (B) LOCATION: 6
        (D) OTHER INFORMATION: /note= "Amino Acid 6 wherein Xaa is
            Arg or Leu."

(ix) FEATURE:
        (A) NAME/KEY: Peptide
        (B) LOCATION: 13
        (D) OTHER INFORMATION: /note= "Amino Acid 13 wherein Xaa
            is Glu or Gly."

(ix) FEATURE:
        (A) NAME/KEY: Peptide
        (B) LOCATION: 16
        (D) OTHER INFORMATION: /note= "Amino Acid 16 wherein Xaa
            is Ser or Arg."

```
          (x) PUBLICATION INFORMATION:
              (H) DOCUMENT NUMBER: WO 92/13884
              (J) PUBLICATION DATE: 20-AUG-1992

(xi) SEQUENCE DESCRIPTION: SEQ ID NO:17:

Leu Glu Gln Xaa Arg Xaa Ala Lys Glu Lys Leu Gln Xaa Gln Gln Xaa
1               5                   10                  15

Asp (2) INFORMATION FOR SEQ ID NO:18:

(i) SEQUENCE CHARACTERISTICS:
              (A) LENGTH: 17 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 5
              (D) OTHER INFORMATION: /note= "Amino Acid 5 wherein Xaa is
                  Glu or Asp."

(ix) FEATURE:
              (A) NAME/KEY: Peptide
              (B) LOCATION: 7
              (D) OTHER INFORMATION: /note= "Amino Acid 7 wherein Xaa is
                  Arg or Leu."

(ix) FEATURE:
              (A) NAME/KEY: Peptide
              (B) LOCATION: 14
              (D) OTHER INFORMATION: /note= "Amino Acid 14 wherein Xaa
                  is Glu or Gly."

(ix) FEATURE:
              (A) NAME/KEY: Peptide
              (B) LOCATION: 17
              (D) OTHER INFORMATION: /note= "Amino Acid 17 wherein Xaa
                  is Ser or Arg."

(x) PUBLICATION INFORMATION:
              (H) DOCUMENT NUMBER: WO 92/13884
              (J) PUBLICATION DATE: 20-AUG-1992

(xi) SEQUENCE DESCRIPTION: SEQ ID NO:18:

Asp Leu Glu Gln Xaa Arg Xaa Ala Lys Glu Lys Leu Gln Xaa Gln Gln
1               5                   10                  15

Xaa (2) INFORMATION FOR SEQ ID NO:19:

(i) SEQUENCE CHARACTERISTICS:
              (A) LENGTH: 107 amino acids
              (B) TYPE: amino acid
              (C) STRANDEDNESS: single
              (D) TOPOLOGY: linear (ii) MOLECULE TYPE: peptide (x) PUBLICATION INFORMATION:
              (H) DOCUMENT NUMBER: WO 92/13884
              (J) PUBLICATION DATE: 20-AUG-1992

(xi) SEQUENCE DESCRIPTION: SEQ ID NO:19:

Arg Lys Ala Asp Thr Lys Lys Asn Leu Glu Arg Lys Lys Glu His Gly
1               5                   10                  15

Asp Ile Leu Ala Glu Asp Leu Tyr Gly Arg Leu Glu Ile Pro Ala Ile
```

```
                20              25              30
Glu Leu Pro Ser Glu Asn Glu Arg Gly Tyr Tyr Ile Pro His Gln Ser
            35              40              45
Ser Leu Pro Gln Asp Asn Arg Gly Asn Ser Arg Asp Ser Lys Glu Ile
50              55              60
Ser Ile Ile Glu Lys Thr Asn Arg Glu Ser Ile Thr Thr Asn Val Glu
65              70              75              80
Gly Arg Arg Asp Ile His Lys Gly His Leu Glu Lys Lys Asp Gly
                85              90              95
Ser Ile Lys Pro Glu Gln Lys Glu Asp Lys Ser
            100             105
```

(2) INFORMATION FOR SEQ ID NO:20:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:20:

```
Leu Gln Glu Gln Gln Arg Asp Leu Glu Gln Arg Lys Ala Asp Thr Lys
1               5               10              15
Lys Asn Leu Glu Arg Lys Lys Glu His Gly Asp Ile Leu Ala Glu Asp
            20              25              30
Leu Tyr Gly Arg Leu Glu Ile Pro Ala Ile Glu Leu Pro Ser Glu Asn
            35              40              45
Glu Arg Gly Tyr Tyr Ile Pro His Gln Ser Ser Leu Pro Gln Asp Asn
        50              55              60
Arg Gly Asn Ser Arg Asp Ser Lys Glu Ile Ser Ile Ile Glu Lys Thr
65              70              75              80
Asn Arg Glu Ser Ile Thr Thr Asn Val Glu Gly Arg Arg Asp Ile His
            85              90              95
Lys Gly His Leu Glu Lys Lys Asp Gly Ser Ile Lys Pro Glu Gln
            100             105             110
Lys Glu Asp Lys Ser
        115
```

(2) INFORMATION FOR SEQ ID NO:21:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:21:

```
Asp Thr Lys Lys Asn Leu Glu Arg Lys Lys Glu His Gly Asp Ile Leu
1               5               10              15
Ala Glu Asp Leu Tyr Gly Arg Leu Glu Ile Pro
```

```
                20                  25

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:22:

Glu Arg Arg Ala Lys Glu Lys Leu Gln Glu Gln Gln Arg Asp Leu Glu
1               5                   10                  15

Gln Arg Lys Ala Asp Thr Lys Lys
            20

(2) INFORMATION FOR SEQ ID NO:23:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:23:

Asn Ser Arg Asp Ser Lys Glu Ile Ser Ile Ile Glu Lys Thr Asn Arg
1               5                   10                  15

Glu Ser Ile Thr Thr Asn Val Glu Gly Arg Arg Asp Ile His Lys
            20                  25                  30

(2) INFORMATION FOR SEQ ID NO:24:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:24:

Arg Asp Glu Leu Phe Asn Glu Leu Leu Asn Ser Val Asp Val Asn Gly
1               5                   10                  15

Glu Val Lys Glu Asn Ile Leu Glu Glu Ser Gln Val Asn Asp Asp Ile
            20                  25                  30

Phe Asn Ser Leu Val Lys Ser Val Gln Gln Glu Gln Gln His Asn Val
        35                  40                  45

Glu Glu Lys Val Glu Glu Ser Val Glu Glu Asn Asp Glu Glu Ser Val
    50                  55                  60

Glu Glu Asn Val Glu Glu Asn Val Glu Glu Asn Asp Asp Gly Ser Val
65                  70                  75                  80
```

```
Ala Ser Ser Val Glu Glu Ser Ile Ala Ser Ser Val Asp Glu Ser Ile
                85                  90                  95

Asp Ser Ser Ile Glu Glu Asn Val Ala Pro Thr Val Glu Glu Ile Val
            100                 105                 110

Ala Pro Thr Val Glu Glu Ile Val Ala Pro Ser Val Val Glu Lys Cys
        115                 120                 125

Ala Pro Ser Val Glu Glu Ser Val Ala Pro Ser Val Glu Glu Ser Val
    130                 135                 140

Ala Glu Met Leu Lys Glu Arg
145                 150
```

(2) INFORMATION FOR SEQ ID NO:25:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:25:

```
Arg Asp Glu Leu Phe Asn Glu Leu Leu Asn Ser Val Asp Val Asn Gly
1               5                   10                  15

Glu Val Lys Glu Asn Ile Leu Glu Glu Ser Gln Val Asn Asp Asp Ile
            20                  25                  30

Phe Asn Ser Leu Val Lys Ser Val Gln Gln Glu Gln Gln His Asn
        35                  40                  45
```

(2) INFORMATION FOR SEQ ID NO:26:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:26:

```
Asp Glu Leu Phe Asn Glu Leu Leu Asn Ser Val Asp Val Asn Gly Glu
1               5                   10                  15

Val Lys Glu Asn Ile Leu Glu Glu Ser Gln
            20                  25
```

(2) INFORMATION FOR SEQ ID NO:27:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:27:

Leu Glu Glu Ser Gln Val Asn Asp Asp Ile Phe Ser Asn Ser Leu Val
1               5                   10                  15

Lys Ser Val Gln Gln Glu Gln Gln His Asn Val
            20                  25

(2) INFORMATION FOR SEQ ID NO:28:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:28:

Val Glu Lys Cys Ala Pro Ser Val Glu Glu Ser Val Ala Pro Ser Val
1               5                   10                  15

Glu Glu Ser Val Ala Glu Met Leu Lys Glu Arg
            20                  25

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:29:

TTGTTCTAGA TCGCTTT                                                    17

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:30:

AAAGAAGATA AATCT                                                      15

(2) INFORMATION FOR SEQ ID NO:31:

(i) SEQUENCE CHARACTERISTICS:
        (A) LENGTH: 316 amino acids
        (B) TYPE: amino acid
        (C) STRANDEDNESS: single
        (D) TOPOLOGY: linear (ii) MOLECULE TYPE: peptide (x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:31:

Ser Asp Leu Glu Gln Glu Arg Arg Ala Lys Glu Lys Leu Gln Glu Gln
1               5                   10                  15

Gln Ser Asp Leu Glu Gln Asp Arg Leu Ala Lys Glu Lys Leu Gln Glu
                20                  25                  30

Gln Gln Ser Asp Leu Glu Gln Glu Arg Arg Ala Lys Glu Lys Leu Gln
            35                  40                  45

Glu Gln Gln Ser Asp Leu Glu Gln Glu Arg Arg Ala Lys Glu Lys Leu
50                  55                  60

Gln Gln Gln Gln Ser Asp Leu Glu Gln Glu Arg Arg Ala Lys Glu Lys
65                  70                  75                  80

Leu Gln Glu Gln Gln Ser Asp Leu Glu Gln Asp Arg Leu Ala Lys Glu
                85                  90                  95

Lys Leu Gln Glu Gln Gln Ser Asp Leu Glu Gln Glu Arg Arg Ala Lys
                100                 105                 110

Glu Lys Leu Gln Glu Gln Gln Ser Asp Leu Glu Gln Glu Arg Arg Ala
                115                 120                 125

Lys Glu Lys Leu Gln Glu Gln Gln Ser Asp Leu Glu Gln Glu Arg Arg
                130                 135                 140

Ala Lys Glu Lys Leu Gln Glu Gln Gln Ser Asp Leu Glu Gln Glu Arg
145                 150                 155                 160

Arg Ala Lys Glu Lys Leu Gln Glu Gln Gln Ser Asp Leu Glu Gln Glu
                165                 170                 175

Arg Arg Ala Lys Glu Lys Leu Gln Glu Gln Gln Ser Asp Leu Glu Gln
                180                 185                 190

Glu Arg Arg Ala Lys Glu Lys Leu Gln Glu Gln Gln Arg Asp Leu Glu
                195                 200                 205

Gln Arg Lys Ala Asp Thr Lys Lys Asn Leu Glu Arg Lys Lys Glu His
                210                 215                 220

Gly Asp Ile Leu Ala Glu Asp Leu Tyr Gly Arg Leu Glu Ile Pro Ala
225                 230                 235                 240

Ile Glu Leu Pro Ser Glu Asn Glu Arg Gly Tyr Tyr Ile Pro His Gln
                245                 250                 255

Ser Ser Leu Pro Gln Asp Asn Arg Gly Asn Ser Arg Asp Ser Lys Glu
                260                 265                 270

Ile Ser Ile Ile Glu Lys Thr Asn Arg Glu Ser Ile Thr Thr Asn Val
                275                 280                 285

Glu Gly Arg Arg Asp Ile His Lys Gly His Leu Glu Glu Lys Lys Asp
                290                 295                 300

Gly Ser Ile Lys Pro Glu Gln Lys Glu Asp Lys Ser
305                 310                 315

(2) INFORMATION FOR SEQ ID NO:32:

(i) SEQUENCE CHARACTERISTICS:
        (A) LENGTH: 950 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:32:

AAAGCGATCT AGAACAAGAG AGACGTGCTA AAGAAAAGTT GCAAGAACAA CAAAGCGATT      60

TAGAACAAGA TAGACTTGCT AAAGAAAAGT TACAAGAGCA GCAAAGCGAT TTAGAACAAG     120

AGAGACTTGC TAAAGAAAAG TTGCAAGAAC AACAAAGCGA TCTAGAACAA GAGAGACGTG     180

CTAAAGAAAA GTTGCAAGAA CAACAAAGCG ATTTAGAACA AGAGAGACGT GCTAAAGAAA     240

AGTTGCAAGA ACAACAAAGC GATTTAGAAC AAGATAGACT TGCTAAAGAA AAGTTACAAG     300

AGCAGCAAAG CGATTTAGAA CAAGAGAGAC GTGCTAAAGA AAAGTTGCAA GAACAACAAA     360

GCGATTTAGA ACAAGAGAGA CGTGCTAAAG AAAAGTTGCA AGAACAACAA AGCGATTTAG     420

AACAAGAGAG ACTTGCTAAA GAAAGTTGC AAGAACAACA AAGCGATTTA GAACAAGAGA      480

GACGTGCTAA AGAAAGTTG CAAGAACAAC AAAGCGATTT AGAACAAGAG AGACGTGCTA      540

AAGAAAAGTT GCAAGAACAA CAAAGCGATT TAGAACAAGA GAGACGTGCT AAAGAAAAGT     600

TGCAAGAGCA GCAAAGAGAT TTAGAACAAA GGAAGGCTGA TACGAAAAAA AATTTAGAAA     660

GAAAAAGGA ACATGGAGAT ATATTAGCAG AGGATTTATA TGGTCGTTTA GAAATACCAG      720

CTATAGAACT TCCATCAGAA AATGAACGTG GATATTATAT ACCACATCAA TCTTCTTTAC     780

CTCAGGACAA CAGAGGGAAT AGTAGAGATT CCAAGGAAAT ATCTATAATA GAAAAAACAA     840

ATAGAGAATC TATTACAACA AATGTTGAAG GACGAAGGGA TATACATAAA GGACATCTTG     900

AAGAAAAGAA AGATGGTTCA ATAAAACCAG AACAAAAAGA AGATAAATCT                950

(2) INFORMATION FOR SEQ ID NO:33:

(i) SEQUENCE CHARACTERISTICS:
        (A) LENGTH: 464 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:33:

GAATTCCGTG ATGAACTTTT TAATGAATTA TTAAATAGTG TAGATGTTAA TGGAGAAGTA      60

AAAGAAAATA TTTTGGAGGA AAGTCAAGTT AATGACGATA TTTTTAATAG TTTAGTAAAA     120

AGTGTTCAAC AAGAACAACA ACACAATGTT GAAGAAAAAG TTGAAGAAAG TGTAGAAGAA     180

AATGACGAAG AAAGTGTAGA AGAAAATGTA GAAGAAATG TAGAAGAAAA TGACGACGGA      240

AGTGTAGCCT CAAGTGTTGA AGAAAGTATA GCTTCAAGTG TTGATGAAAG TATAGATTCA     300

AGTATTGAAG AAAATGTAGC TCCAACTGTT GAAGAAATCG TAGCTCCAAC TGTTGAAGAA     360

ATTGTAGCTC CAAGTGTTGT AGAAAAGTGT GCTCCAAGTG TTGAAGAAAG TGTAGCTCCA     420

AGTGTTGAAG AAAGTGTAGC TGAAATGTTG AAGGAAAGGA ATTC                      464

(2) INFORMATION FOR SEQ ID NO:34:

(i) SEQUENCE CHARACTERISTICS:
        (A) LENGTH: 988 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
            (H) DOCUMENT NUMBER: WO 92/13884
            (J) PUBLICATION DATE: 20-AUG-1992

(xi) SEQUENCE DESCRIPTION: SEQ ID NO:34:

```
AAAGTATACA TCTTCCTTCT TTACTTCTTA AAATGAAACA TATTTTGTAC ATATCATTTT      60
ACTTTATCCT TGTTAATTTA TTGATATTTC ATATAAATGG AAAGATAATA AAGAATTCTG     120
AAAAAGATGA AATCATAAAA TCTAACTTGA GAAGTGGTTC TTCAAATTCT AGGAATCGAA     180
TAAATGAGGA AAATCACGAG AAGAAACACG TTTTATCTCA TAATTCATAT GAGAAAACTA     240
AAAATAATGA AATAATAAA TTTTTCGATA AGGATAAAGA GTTAACGATG TCTAATGTAA      300
AAAATGTGTC ACAAACAAAT TTCAAAGTC TTTTAAGAAA TCTTGGTGTT TCAGAGAATA      360
TATTCCTTAA AGAAAATAAA TTAAATAAGG AAGGGAAATT AATTGAACAC ATAATAAATG     420
ATGATGACGA TAAAAAAAAA TATATTAAAG GGCAAGACGA AAACAGACAA GAAGATCTTG     480
AAGAAAAAGC AGCTAAAGAA AAGTTACAGG GGCAACAAAG CGATTCAGAA CAAGAGAGAC     540
GTGCTAAAGA AAAGTTGCAA GAACAACAAA GCGATTTAGA ACAAGAGAGA CTTGCTAAAG     600
AAAAGTTGCA AGAACAACAA AGCGATTTAG AACAAGAGAG ACGTGCTAAA GAAAAGTTGC     660
AAGAACAACA AAGCGATTTA GAACAAGAGA GACTTGCTAA AGAAAAGTTG CAAGAACAAC     720
AAAGCGATTT AGAACAAGAG AGACGTGCTA AAGAAAAGTT GCAAGAACAA CAAAGCGATT     780
TAGAACAAGA GAGACGTGCT AAAGAAAAGT TGCAAGAACA ACAAAGCGAT TTAGAACAAG     840
AGAGACTTGC TAAAGAAAAG TTACAAGAGC AGCAAAGCGA TTTAGAACAA GATAGACTTG     900
CTAAAGAAAA GTTGCAAGAA CAACAAAGCG ATTTAGAACA AGAGAGACGT GCTAAAGAAA     960
GGTTGCAAGA ACAACAAAGC GATTTAGA                                        988
```

(2) INFORMATION FOR SEQ ID NO:35:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:35:

```
ATGAAACATA TT                                                          12
```

(2) INFORMATION FOR SEQ ID NO:36:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:36:

```
AAGCGATTTA GA                                                              12
```

(2) INFORMATION FOR SEQ ID NO:37:

(i) SEQUENCE CHARACTERISTICS:
        (A) LENGTH: 954 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..954

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:37:

```
ATG AAA CAT ATT TTG TAC ATA TCA TTT TAC TTT ATC CTT GTT AAT TTA        48
Met Lys His Ile Leu Tyr Ile Ser Phe Tyr Phe Ile Leu Val Asn Leu
 1               5                  10                  15

TTG ATA TTT CAT ATA AAT GGA AAG ATA ATA AAG AAT TCT GAA AAA GAT        96
Leu Ile Phe His Ile Asn Gly Lys Ile Ile Lys Asn Ser Glu Lys Asp
            20                  25                  30

GAA ATC ATA AAA TCT AAC TTG AGA AGT GGT TCT TCA AAT TCT AGG AAT       144
Glu Ile Ile Lys Ser Asn Leu Arg Ser Gly Ser Ser Asn Ser Arg Asn
    35                  40                  45

CGA ATA AAT GAG GAA AAT CAC GAG AAG AAA CAC GTT TTA TCT CAT AAT       192
Arg Ile Asn Glu Glu Asn His Glu Lys Lys His Val Leu Ser His Asn
50                  55                  60

TCA TAT GAG AAA ACT AAA AAT AAT GAA AAT AAT AAA TTT TTC GAT AAG       240
Ser Tyr Glu Lys Thr Lys Asn Asn Glu Asn Asn Lys Phe Phe Asp Lys
 65                  70                  75                  80

GAT AAA GAG TTA ACG ATG TCT AAT GTA AAA AAT GTG TCA CAA ACA AAT       288
Asp Lys Glu Leu Thr Met Ser Asn Val Lys Asn Val Ser Gln Thr Asn
                 85                  90                  95

TTC AAA AGT CTT TTA AGA AAT CTT GGT GTT TCA GAG AAT ATA TTC CTT       336
Phe Lys Ser Leu Leu Arg Asn Leu Gly Val Ser Glu Asn Ile Phe Leu
            100                 105                 110

AAA GAA AAT AAA TTA AAT AAG GAA GGG AAA TTA ATT GAA CAC ATA ATA       384
Lys Glu Asn Lys Leu Asn Lys Glu Gly Lys Leu Ile Glu His Ile Ile
        115                 120                 125

AAT GAT GAT GAC GAT AAA AAA AAA TAT ATT AAA GGG CAA GAC GAA AAC       432
Asn Asp Asp Asp Asp Lys Lys Lys Tyr Ile Lys Gly Gln Asp Glu Asn
    130                 135                 140

AGA CAA GAA GAT CTT GAA GAA AAA GCA GCT AAA GAA AAG TTA CAG GGG       480
Arg Gln Glu Asp Leu Glu Glu Lys Ala Ala Lys Glu Lys Leu Gln Gly
145                 150                 155                 160

CAA CAA AGC GAT TCA GAA CAA GAG AGA CGT GCT AAA GAA AAG TTG CAA       528
Gln Gln Ser Asp Ser Glu Gln Glu Arg Arg Ala Lys Glu Lys Leu Gln
                165                 170                 175

GAA CAA CAA AGC GAT TTA GAA CAA GAG AGA CTT GCT AAA GAA AAG TTG       576
Glu Gln Gln Ser Asp Leu Glu Gln Glu Arg Leu Ala Lys Glu Lys Leu
            180                 185                 190

CAA GAA CAA CAA AGC GAT TTA GAA CAA GAG AGA CGT GCT AAA GAA AAG       624
Gln Glu Gln Gln Ser Asp Leu Glu Gln Glu Arg Arg Ala Lys Glu Lys
        195                 200                 205

TTG CAA GAA CAA CAA AGC GAT TTA GAA CAA GAG AGA CTT GCT AAA GAA       672
Leu Gln Glu Gln Gln Ser Asp Leu Glu Gln Glu Arg Leu Ala Lys Glu
    210                 215                 220
```

-continued

```
AAG TTG CAA GAA CAA CAA AGC GAT TTA GAA CAA GAG AGA CGT GCT AAA      720
Lys Leu Gln Glu Gln Gln Ser Asp Leu Glu Gln Glu Arg Arg Ala Lys
225                 230                 235                 240

GAA AAG TTG CAA GAA CAA CAA AGC GAT TTA GAA CAA GAG AGA CGT GCT      768
Glu Lys Leu Gln Glu Gln Gln Ser Asp Leu Glu Gln Glu Arg Arg Ala
                245                 250                 255

AAA GAA AAG TTG CAA GAA CAA CAA AGC GAT TTA GAA CAA GAG AGA CTT      816
Lys Glu Lys Leu Gln Glu Gln Gln Ser Asp Leu Glu Gln Glu Arg Leu
            260                 265                 270

GCT AAA GAA AAG TTA CAA GAG CAG CAA AGC GAT TTA GAA CAA GAT AGA      864
Ala Lys Glu Lys Leu Gln Glu Gln Gln Ser Asp Leu Glu Gln Asp Arg
        275                 280                 285

CTT GCT AAA GAA AAG TTG CAA GAA CAA CAA AGC GAT TTA GAA CAA GAG      912
Leu Ala Lys Glu Lys Leu Gln Glu Gln Gln Ser Asp Leu Glu Gln Glu
    290                 295                 300

AGA CGT GCT AAA GAA AGG TTG CAA GAA CAA CAA AGC GAT TTA              954
Arg Arg Ala Lys Glu Arg Leu Gln Glu Gln Gln Ser Asp Leu
305                 310                 315
```

(2) INFORMATION FOR SEQ ID NO:38:

(i) SEQUENCE CHARACTERISTICS:
        (A) LENGTH: 1493 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:38:

```
CAAGAACAAC AAAGCGATCT AGAACAAGAG AGACGTGCTA AGAAAAGTT GCAAGAACAA      60
CAAAGCGATT TAGAACAAGA TAGACTTGCT AAAGAAAAGT TACAAGAGCA GCAAAGCGAT    120
TTAGAACAAG AGAGACTTGC TAAGAAAAGT TGCAAGAACA ACAAAGCGAT CTAGAACAAG    180
AGAGACGTGC TAAAGAAAAG TTGCAAGAAC AACAAAGCGA TTTAGAACAA GAGAGACGTG    240
CTAAAGAAAA GTTGCAAGAA CAACAAAGCG ATTTAGAACA AGATAGACTT GCTAAAGAAA    300
AGTTACAAGA GCAGCAAAGC GATTTAGAAC AAGAGAGACG TGCTAAAGAA AAGTTGCAAG    360
AACAACAAAG CGATTTAGAA CAAGAGAGAC GTGCTAAGAA AAGTTGCAAG AACAACAAAG    420
CGATTTAGAA CAAGAGAGAC TTGCTAAAGA AAAGTTGCAA GAACAACAAA GCGATTTAGA    480
ACAAGAGAGA CGTGCTAAAG AAAAGTTGCA AGAACAACAA AGCGATTTAG AACAAGAGAG    540
ACGTGCTAAG AAAAGTTGCA AGAACAACAA AGCGATTTAG AACAAGAGAG ACGTGCTAAA    600
GAAAAGTTGC AAGAGCAGCA AAGAGATTTA GAACAAAGGA AGGCTGATAC GAAAAAAAAT    660
TTAGAAAGAA AAAAGGAACA TGGAGATATA TTAGCAGAGG ATTTATATGG TCGTTTAGAA    720
ATACCAGCTA TAGAACTTCC ATCAGAAAAT GAACGTGGAT ATTATATACC ACATCAATCT    780
TCTTTACCTC AGGACAACAG AGGGAATAGT AGAGATTCCA GGAAATATC TATAATAGAA    840
AAAACAAATA GAGAATCTAT TACAACAAAT GTTGAAGGAC GAAGGGATAT ACATAAAGGA    900
CATCTTGAAG AAAAGAAAGA TGGTTCAATA AAACCAGAAC AAAAGAAGA TAAATCTGCT    960
GACATACAAA ATCATACATT AGAGACAGTA AATATTTCTG ATGTTAATGA TTTTCAAATA   1020
AGTAAGTATG AGGATGAAAT AAGTGCTGAA TATGACGATT CATTAATAGA TGAAGAAGAA   1080
GATGATGAAG ACTTAGACGA ATTTAAGCCT ATTGTGCAAT ATGACAATTT CCAAGATGAA   1140
```

-continued

```
GAAAACATAG GAATTTATAA AGAACTAGAA GATTTGATAG AGAAAAATGA AAATTTAGAT      1200

GATTTAGATG AAGGAATAGA AAAATCATCA GAAGAATTAT CTGAAGAAAA AATAAAAAAA      1260

GGAAAGAAAT ATGAAAAAAC AAAGGATAAT AATTTTAAAC CAAATGATAA AGTTTGTAT       1320

GATGAGCATA TTAAAAAATA TAAAAATGAT AAGCAGGTTA ATAAGGAAAA GGAAAAATTC      1380

ATAAAATCAT TGTTTCATAT ATTTGACGGA GACAATGAAA TTTTACAGAT CGTGGATGAG      1440

TTATCTGAAG ATATAACTAA ATATTTTATG AAACTATAAA AGGTTATATA TTT            1493
```

(2) INFORMATION FOR SEQ ID NO:39:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:39:

```
CAAGAACAAC AA                                                           12
```

(2) INFORMATION FOR SEQ ID NO:40:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:40:

```
GGTTATATAT TT                                                           12
```

(2) INFORMATION FOR SEQ ID NO:41:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1482

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:41:

```
CAA GAA CAA CAA AGC GAT CTA GAA CAA GAG AGA CGT GCT AAA GAA AAG         48
Gln Glu Gln Gln Ser Asp Leu Glu Gln Glu Arg Arg Ala Lys Glu Lys
  1               5                  10                  15

TTG CAA GAA CAA CAA AGC GAT TTA GAA CAA GAT AGA CTT GCT AAA GAA         96
Leu Gln Glu Gln Gln Ser Asp Leu Glu Gln Asp Arg Leu Ala Lys Glu
             20                  25                  30
```

-continued

| | | |
|---|---|---|
| AAG TTA CAA GAG CAG CAA AGC GAT TTA GAA CAA GAG AGA CTT GCT AAA<br>Lys Leu Gln Glu Gln Gln Ser Asp Leu Glu Gln Glu Arg Leu Ala Lys<br>35                   40                     45 | 144 |
| GAA AAG TTG CAA GAA CAA CAA AGC GAT CTA GAA CAA GAG AGA CGT GCT<br>Glu Lys Leu Gln Glu Gln Gln Ser Asp Leu Glu Gln Glu Arg Arg Ala<br>50                   55                   60 | 192 |
| AAA GAA AAG TTG CAA GAA CAA CAA AGC GAT TTA GAA CAA GAG AGA CGT<br>Lys Glu Lys Leu Gln Glu Gln Gln Ser Asp Leu Glu Gln Glu Arg Arg<br>65                  70                  75                 80 | 240 |
| GCT AAA GAA AAG TTG CAA GAA CAA CAA AGC GAT TTA GAA CAA GAT AGA<br>Ala Lys Glu Lys Leu Gln Glu Gln Gln Ser Asp Leu Glu Gln Asp Arg<br>85                  90                  95 | 288 |
| CTT GCT AAA GAA AAG TTA CAA GAG CAG CAA AGC GAT TTA GAA CAA GAG<br>Leu Ala Lys Glu Lys Leu Gln Glu Gln Gln Ser Asp Leu Glu Gln Glu<br>          100                  105                110 | 336 |
| AGA CGT GCT AAA GAA AAG TTG CAA GAA CAA CAA AGC GAT TTA GAA CAA<br>Arg Arg Ala Lys Glu Lys Leu Gln Glu Gln Gln Ser Asp Leu Glu Gln<br>          115                  120                125 | 384 |
| GAG AGA CGT GCT AAA GAA AAG TTG CAA GAA CAA CAA AGC GAT TTA GAA<br>Glu Arg Arg Ala Lys Glu Lys Leu Gln Glu Gln Gln Ser Asp Leu Glu<br>130                 135                 140 | 432 |
| CAA GAG AGA CTT GCT AAA GAA AAG TTG CAA GAA CAA CAA AGC GAT TTA<br>Gln Glu Arg Leu Ala Lys Glu Lys Leu Gln Glu Gln Gln Ser Asp Leu<br>145                 150                 155                160 | 480 |
| GAA CAA GAG AGA CGT GCT AAA GAA AAG TTG CAA GAA CAA CAA AGC GAT<br>Glu Gln Glu Arg Arg Ala Lys Glu Lys Leu Gln Glu Gln Gln Ser Asp<br>          165                  170                175 | 528 |
| TTA GAA CAA GAG AGA CGT GCT AAA GAA AAG TTG CAA GAA CAA CAA AGC<br>Leu Glu Gln Glu Arg Arg Ala Lys Glu Lys Leu Gln Glu Gln Gln Ser<br>          180                  185                190 | 576 |
| GAT TTA GAA CAA GAG AGA CGT GCT AAA GAA AAG TTG CAA GAG CAG CAA<br>Asp Leu Glu Gln Glu Arg Arg Ala Lys Glu Lys Leu Gln Glu Gln Gln<br>          195                  200                205 | 624 |
| AGA GAT TTA GAA CAA AGG AAG GCT GAT ACG AAA AAA AAT TTA GAA AGA<br>Arg Asp Leu Glu Gln Arg Lys Ala Asp Thr Lys Lys Asn Leu Glu Arg<br>210                 215                 220 | 672 |
| AAA AAG GAA CAT GGA GAT ATA TTA GCA GAG GAT TTA TAT GGT CGT TTA<br>Lys Lys Glu His Gly Asp Ile Leu Ala Glu Asp Leu Tyr Gly Arg Leu<br>225                 230                 235                240 | 720 |
| GAA ATA CCA GCT ATA GAA CTT CCA TCA GAA AAT GAA CGT GGA TAT TAT<br>Glu Ile Pro Ala Ile Glu Leu Pro Ser Glu Asn Glu Arg Gly Tyr Tyr<br>          245                  250                255 | 768 |
| ATA CCA CAT CAA TCT TCT TTA CCT CAG GAC AAC AGA GGG AAT AGT AGA<br>Ile Pro His Gln Ser Ser Leu Pro Gln Asp Asn Arg Gly Asn Ser Arg<br>          260                  265                270 | 816 |
| GAT TCC AAG GAA ATA TCT ATA ATA GAA AAA ACA AAT AGA GAA TCT ATT<br>Asp Ser Lys Glu Ile Ser Ile Ile Glu Lys Thr Asn Arg Glu Ser Ile<br>          275                  280                285 | 864 |
| ACA ACA AAT GTT GAA GGA CGA AGG GAT ATA CAT AAA GGA CAT CTT GAA<br>Thr Thr Asn Val Glu Gly Arg Arg Asp Ile His Lys Gly His Leu Glu<br>290                 295                 300 | 912 |
| GAA AAG AAA GAT GGT TCA ATA AAA CCA GAA CAA AAA GAA GAT AAA TCT<br>Glu Lys Lys Asp Gly Ser Ile Lys Pro Glu Gln Lys Glu Asp Lys Ser<br>305                 310                 315                320 | 960 |
| GCT GAC ATA CAA AAT CAT ACA TTA GAG ACA GTA AAT ATT TCT GAT GTT<br>Ala Asp Ile Gln Asn His Thr Leu Glu Thr Val Asn Ile Ser Asp Val<br>          325                  330                335 | 1008 |
| AAT GAT TTT CAA ATA AGT AAG TAT GAG GAT GAA ATA AGT GCT GAA TAT<br>Asn Asp Phe Gln Ile Ser Lys Tyr Glu Asp Glu Ile Ser Ala Glu Tyr<br>          340                  345                350 | 1056 |

```
GAC GAT TCA TTA ATA GAT GAA GAA GAA GAT GAT GAA GAC TTA GAC GAA    1104
Asp Asp Ser Leu Ile Asp Glu Glu Glu Asp Asp Glu Asp Leu Asp Glu
        355                 360                 365

TTT AAG CCT ATT GTG CAA TAT GAC AAT TTC CAA GAT GAA GAA AAC ATA    1152
Phe Lys Pro Ile Val Gln Tyr Asp Asn Phe Gln Asp Glu Glu Asn Ile
    370                 375                 380

GGA ATT TAT AAA GAA CTA GAA GAT TTG ATA GAG AAA AAT GAA AAT TTA    1200
Gly Ile Tyr Lys Glu Leu Glu Asp Leu Ile Glu Lys Asn Glu Asn Leu
385                 390                 395                 400

GAT GAT TTA GAT GAA GGA ATA GAA AAA TCA TCA GAA GAA TTA TCT GAA    1248
Asp Asp Leu Asp Glu Gly Ile Glu Lys Ser Ser Glu Glu Leu Ser Glu
        405                 410                 415

GAA AAA ATA AAA AAA GGA AAG AAA TAT GAA AAA ACA AAG GAT AAT AAT    1296
Glu Lys Ile Lys Lys Gly Lys Lys Tyr Glu Lys Thr Lys Asp Asn Asn
    420                 425                 430

TTT AAA CCA AAT GAT AAA AGT TTG TAT GAT GAG CAT ATT AAA AAA TAT    1344
Phe Lys Pro Asn Asp Lys Ser Leu Tyr Asp Glu His Ile Lys Lys Tyr
435                 440                 445

AAA AAT GAT AAG CAG GTT AAT AAG GAA AAG GAA AAA TTC ATA AAA TCA    1392
Lys Asn Asp Lys Gln Val Asn Lys Glu Lys Glu Lys Phe Ile Lys Ser
        450                 455                 460

TTG TTT CAT ATA TTT GAC GGA GAC AAT GAA ATT TTA CAG ATC GTG GAT    1440
Leu Phe His Ile Phe Asp Gly Asp Asn Glu Ile Leu Gln Ile Val Asp
465                 470                 475                 480

GAG TTA TCT GAA GAT ATA ACT AAA TAT TTT ATG AAA CTA TAA            1482
Glu Leu Ser Glu Asp Ile Thr Lys Tyr Phe Met Lys Leu
                    485                 490

(2) INFORMATION FOR SEQ ID NO:42:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..12

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:42:

AAG GTT ATA TAT                                                      12
Lys Val Ile Tyr
  1

(2) INFORMATION FOR SEQ ID NO:43:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:43:
```

-continued

```
CAAGAACAAC AA                                                   12
```

(2) INFORMATION FOR SEQ ID NO:44:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:44:

```
ATGAAACTAT AA                                                   12
```

(2) INFORMATION FOR SEQ ID NO:45:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1482

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:45:

```
CAA GAA CAA CAA AGC GAT CTA GAA CAA GAG AGA CGT GCT AAA GAA AAG    48
Gln Glu Gln Gln Ser Asp Leu Glu Gln Glu Arg Arg Ala Lys Glu Lys
 1               5                  10                  15

TTG CAA GAA CAA CAA AGC GAT TTA GAA CAA GAT AGA CTT GCT AAA GAA    96
Leu Gln Glu Gln Gln Ser Asp Leu Glu Gln Asp Arg Leu Ala Lys Glu
             20                  25                  30

AAG TTA CAA GAG CAG CAA AGC GAT TTA GAA CAA GAG AGA CTT GCT AAA   144
Lys Leu Gln Glu Gln Gln Ser Asp Leu Glu Gln Glu Arg Leu Ala Lys
         35                  40                  45

GAA AAG TTG CAA GAA CAA CAA AGC GAT CTA GAA CAA GAG AGA CGT GCT   192
Glu Lys Leu Gln Glu Gln Gln Ser Asp Leu Glu Gln Glu Arg Arg Ala
     50                  55                  60

AAA GAA AAG TTG CAA GAA CAA CAA AGC GAT TTA GAA CAA GAG AGA CGT   240
Lys Glu Lys Leu Gln Glu Gln Gln Ser Asp Leu Glu Gln Glu Arg Arg
 65                  70                  75                  80

GCT AAA GAA AAG TTG CAA GAA CAA CAA AGC GAT TTA GAA CAA GAT AGA   288
Ala Lys Glu Lys Leu Gln Glu Gln Gln Ser Asp Leu Glu Gln Asp Arg
                 85                  90                  95

CTT GCT AAA GAA AAG TTA CAA GAG CAG CAA AGC GAT TTA GAA CAA GAG   336
Leu Ala Lys Glu Lys Leu Gln Glu Gln Gln Ser Asp Leu Glu Gln Glu
            100                 105                 110

AGA CGT GCT AAA GAA AAG TTG CAA GAA CAA CAA AGC GAT TTA GAA CAA   384
Arg Arg Ala Lys Glu Lys Leu Gln Glu Gln Gln Ser Asp Leu Glu Gln
        115                 120                 125

GAG AGA CGT GCT AAA GAA AAG TTG CAA GAA CAA CAA AGC GAT TTA GAA   432
Glu Arg Arg Ala Lys Glu Lys Leu Gln Glu Gln Gln Ser Asp Leu Glu
    130                 135                 140

CAA GAG AGA CTT GCT AAA GAA AAG TTG CAA GAA CAA CAA AGC GAT TTA   480
```

-continued

```
        Gln Glu Arg Leu Ala Lys Glu Lys Leu Gln Glu Gln Ser Asp Leu
        145                 150                 155                 160

GAA CAA GAG AGA CGT GCT AAA GAA AAG TTG CAA GAA CAA CAA AGC GAT        528
Glu Gln Glu Arg Arg Ala Lys Glu Lys Leu Gln Glu Gln Gln Ser Asp
                    165                 170                 175

TTA GAA CAA GAG AGA CGT GCT AAA GAA AAG TTG CAA GAA CAA CAA AGC        576
Leu Glu Gln Glu Arg Arg Ala Lys Glu Lys Leu Gln Glu Gln Gln Ser
                180                 185                 190

GAT TTA GAA CAA GAG AGA CGT GCT AAA GAA AAG TTG CAA GAG CAG CAA        624
Asp Leu Glu Gln Glu Arg Arg Ala Lys Glu Lys Leu Gln Glu Gln Gln
            195                 200                 205

AGA GAT TTA GAA CAA AGG AAG GCT GAT ACG AAA AAA AAT TTA GAA AGA        672
Arg Asp Leu Glu Gln Arg Lys Ala Asp Thr Lys Lys Asn Leu Glu Arg
        210                 215                 220

AAA AAG GAA CAT GGA GAT ATA TTA GCA GAG GAT TTA TAT GGT CGT TTA        720
Lys Lys Glu His Gly Asp Ile Leu Ala Glu Asp Leu Tyr Gly Arg Leu
225                 230                 235                 240

GAA ATA CCA GCT ATA GAA CTT CCA TCA GAA AAT GAA CGT GGA TAT TAT        768
Glu Ile Pro Ala Ile Glu Leu Pro Ser Glu Asn Glu Arg Gly Tyr Tyr
                245                 250                 255

ATA CCA CAT CAA TCT TCT TTA CCT CAG GAC AAC AGA GGG AAT AGT AGA        816
Ile Pro His Gln Ser Ser Leu Pro Gln Asp Asn Arg Gly Asn Ser Arg
            260                 265                 270

GAT TCC AAG GAA ATG TCT ATA ATA GAA AAA ACA AAT AGA GAA TCT ATT        864
Asp Ser Lys Glu Met Ser Ile Ile Glu Lys Thr Asn Arg Glu Ser Ile
        275                 280                 285

ACA ACA AAT GTT GAA GGA CGA AGG GAT ATA CAT AAA GGA CAT CTT GAA        912
Thr Thr Asn Val Glu Gly Arg Arg Asp Ile His Lys Gly His Leu Glu
    290                 295                 300

GAA AAG AAA GAT GGT TCA ATA AAA CCA GAA CAA AAA GAA GAT AAA TCT        960
Glu Lys Lys Asp Gly Ser Ile Lys Pro Glu Gln Lys Glu Asp Lys Ser
305                 310                 315                 320

GCT GAC ATA CAA AAT CAT ACA TTA GAG ACA GTA AAT ATT TCT GAT GTT       1008
Ala Asp Ile Gln Asn His Thr Leu Glu Thr Val Asn Ile Ser Asp Val
                325                 330                 335

AAT GAT TTT CAA ATA AGT AAG TAT GAG GAT GAA ATA AGT GCT GAA TAT       1056
Asn Asp Phe Gln Ile Ser Lys Tyr Glu Asp Glu Ile Ser Ala Glu Tyr
            340                 345                 350

GAC GAT TCA TTA ATA GAT GAA GAA GAA GAT GAT GAA GAC TTA GAC GAA       1104
Asp Asp Ser Leu Ile Asp Glu Glu Glu Asp Asp Glu Asp Leu Asp Glu
        355                 360                 365

TTT AAG CCT ATT GTG CAA TAT GAC AAT TTC CAA GAT GAA GAA AAC ATA       1152
Phe Lys Pro Ile Val Gln Tyr Asp Asn Phe Gln Asp Glu Glu Asn Ile
    370                 375                 380

GGA ATT TAT AAA GAA CTA GAA GAT TTG ATA GAG AAA AAT GAA AAT TTA       1200
Gly Ile Tyr Lys Glu Leu Glu Asp Leu Ile Glu Lys Asn Glu Asn Leu
385                 390                 395                 400

GAT GAT TTA GAT GAA GGA ATA GAA AAA TCA TCA GAA GAA TTA TCT GAA       1248
Asp Asp Leu Asp Glu Gly Ile Glu Lys Ser Ser Glu Glu Leu Ser Glu
                405                 410                 415

GAA AAA ATA AAA AAA GGA AAG AAA TAT GAA AAA ACA AAG GAT AAT AAT       1296
Glu Lys Ile Lys Lys Gly Lys Lys Tyr Glu Lys Thr Lys Asp Asn Asn
            420                 425                 430

TTT AAA CCA AAT GAT AAA AGT TTG TAT GAT GAG CAT ATT AAA AAA TAT       1344
Phe Lys Pro Asn Asp Lys Ser Leu Tyr Asp Glu His Ile Lys Lys Tyr
        435                 440                 445

AAA AAT GAT AAG CAG GTT AAT AAG GAA AAG GAA AAA TTC ATA AAA TCA       1392
Lys Asn Asp Lys Gln Val Asn Lys Glu Lys Glu Lys Phe Ile Lys Ser
    450                 455                 460
```

```
TTG TTT CAT ATA TTT GAC GGA GAC AAT GAA ATT TTA CAG ATC GTG GAT         1440
Leu Phe His Ile Phe Asp Gly Asp Asn Glu Ile Leu Gln Ile Val Asp
465                 470                 475                 480

GAG TTA TCT GAA GAT ATA ACT AAA TAT TTT ATG AAA CTA TAA                 1482
Glu Leu Ser Glu Asp Ile Thr Lys Tyr Phe Met Lys Leu
                485                 490

(2) INFORMATION FOR SEQ ID NO:46:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..12

(x) PUBLICATION INFORMATION:
        (H) DOCUMENT NUMBER: WO 92/13884
        (J) PUBLICATION DATE: 20-AUG-1992

(xi) SEQUENCE DESCRIPTION: SEQ ID NO:46:

AAG GTT ATA TAT                                                           12
Lys Val Ile Tyr
  1
```